United States Patent [19]

Stokbroekx et al.

[11] Patent Number: 5,106,973
[45] Date of Patent: Apr. 21, 1992

[54] PYRIDZAINAMINE DERIVATIVES

[75] Inventors: Raymond A. Stokbroekx, Beerse; Marcel J. M. Van der Aa, Kasterlee; Marcel G. M. Luyckx, Geel; Gilbert A. J. Grauwels, Kessel-Lo, all of Belgium

[73] Assignee: Janssen Pharmaceutica N.V., Beerse, Belgium

[21] Appl. No.: 613,420

[22] Filed: Nov. 15, 1990

Related U.S. Application Data

[60] Division of Ser. No. 269,805, Nov. 9, 1988, Pat. No. 4,992,433, which is a continuation-in-part of Ser. No. 124,530, Nov. 23, 1987, abandoned.

[51] Int. Cl.⁵ .......................... C07D 237/06
[52] U.S. Cl. .................................. 544/238
[58] Field of Search ............ 514/252, 248; 544/238, 544/237

[56] References Cited

U.S. PATENT DOCUMENTS

| | | | |
|---|---|---|---|
| 2,562,036 | 7/1951 | Hultquist | 544/238 |
| 3,753,988 | 8/1973 | Rodway et al. | 544/237 |
| 4,370,328 | 1/1983 | Campbell | 544/237 |
| 4,413,006 | 11/1983 | Kanno et al. | 514/252 |
| 4,624,952 | 11/1986 | Biziere et al. | 514/247 |
| 4,631,280 | 12/1986 | Kan et al. | 514/247 |
| 4,677,106 | 6/1987 | Wermuth et al. | 514/247 |
| 4,710,499 | 12/1987 | Wermuth et al. | 514/247 |
| 4,721,711 | 1/1988 | Chambon | 514/247 |
| 5,001,125 | 3/1991 | Stokbroekx et al. | 514/252 |

FOREIGN PATENT DOCUMENTS

| | | | |
|---|---|---|---|
| 772365 | 7/1972 | Belgium | 514/247 |
| 0320032 | 6/1989 | European Pat. Off. | 544/238 |

OTHER PUBLICATIONS

Burger, Medicinal Chemistry, 2d Ed. Interscience, NY, p. 42 (1960).

*Primary Examiner*—Donald G. Daus
*Attorney, Agent, or Firm*—Charles J. Metz

[57] ABSTRACT

Novel pyridazinamine derivatives having antiviral activity, compositions containing these compounds as active ingredient, and a method of destructing viruses or preventing the growth thereof in warm-blooded animals suffering from diseases caused by these viruses. Processes for preparing said compounds and compositions.

8 Claims, No Drawings

PYRIDZAINAMINE DERIVATIVES

CROSS-REFERENCE TO RELATED APPLICATIONS

This application is a division of application Ser. No. 269,805, filed on Nov. 9, 1988, now U.S. Pat. No. 4,992,433, which was a continuation-in-part of application Ser. No. 124,530, filed on Nov. 23, 1987, now abandoned.

BACKGROUND OF THE INVENTION

In the European Patent Publication No. 156,433 published Oct. 2, 1985, which corresponds to U.S. Ser. No. 702,772, there are described antivirally active pyridazinamines. Further antiviral agents are described in U.S. Pat. No. 4,451,476 and in the European Patent Publication No. 137,242 published Apr. 17, 1985 both containing invariably an isoxazole moiety.

The compounds of the present invention differ from the cited art compounds by the fact that they contain a pyridazinamine moiety which is substituted in a previously undisclosed manner and particularly by their favourable antiviral properties.

DESCRIPTION OF THE INVENTION

The present invention is concerned with pyridazinamines having the formula

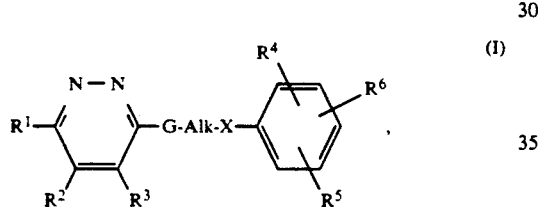

the pharmaceutically acceptable acid addition salts thereof and the stereochemically isomeric forms thereof, wherein $R^1$ is hydrogen, $C_{1-6}$alkyl, halo, hydroxy, mercapto, trifluoromethyl, amino, mono or di($C_{1-6}$alkyl)amino, cyano, $C_{1-6}$alkyloxy, aryloxy, aryl$C_{1-6}$alkyloxy, $C_{1-6}$alkylthio, arylthio, $C_{1-6}$alkylsulfinyl, $C_{1-6}$alkylsulfonyl, arylsulfinyl, arylsulfonyl, $C_{1-6}$alkyloxycarbonyl, $C_{1-6}$alkylcarbonyl or aryl;

$R^2$ and $R^3$ each independently are hydrogen or $C_{1-6}$alkyl, or $R^2$ and $R^3$ combined may form a bivalent radical of formula —CH=CH—CH=CH—

G is a bivalent radical of formula

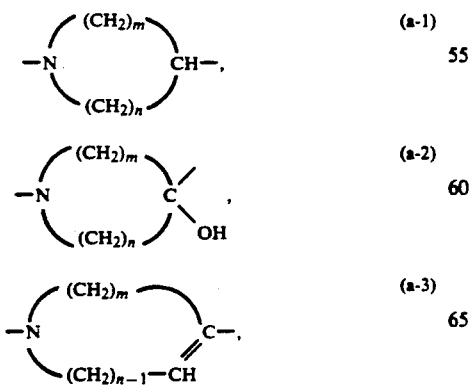

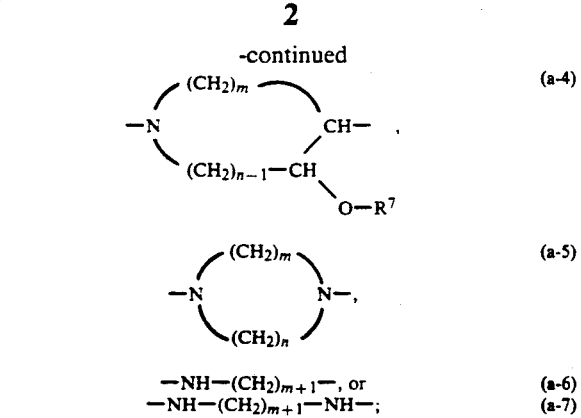

—NH—$(CH_2)_{m+1}$—, or (a-6)
—NH—$(CH_2)_{m+1}$—NH—; (a-7)

wherein one or more carbon atoms within the radicals (a-1) through (a-7) may optionally be substituted with $C_{1-6}$alkyl or two carbon atoms in the radicals (a-1) through (a-5) may be bridged with a $C_{2-4}$alkanediyl radical, m and n each independently are integers of from 1 to 4 inclusive with the proviso that the sum of m and n in the bivalent radicals (a-1) through (a-5) is 3, 4 or 5;

$R^7$ is hydrogen, $C_{1-6}$alkyl or aryl$C_{1-6}$alkyl;

Alk is $C_{1-6}$alkanediyl;

X is O, S, $NR^8$ or a direct bond; said $R^8$ being hydrogen or $C_{1-6}$alkyl;

$R^4$, $R^5$ and $R^6$ each independently are hydrogen, $C_{1-6}$alkyl, hydroxy$C_{1-6}$alkyl, halo, amino, cyano, nitro, $C_{1-6}$alkyloxy, hydroxy, $C_{1-6}$alkylthio, mercapto or trifluoromethyl, in addition and independently from the meaning of $R^4$ and $R^5$, $R^6$ may also be 4,5-dihydro-2-oxazolyl or 2-oxazolyl both being optionally substituted with one or more $C_{1-6}$alkyl or hydroxy$C_{1-6}$alkyl substituents; 5,6-dihydro-4H-1,3-oxazin-2-yl or 4H-1,3-oxazin-2-yl both being optionally substituted with one or more $C_{1-6}$alkyl or hydroxy-$C_{1-6}$alkyl substituents; aryl; or a radical of formula

wherein $Z^1$ is O, S, $NR^9$, $CH_2$ or a direct bond;

$Z^2$ is O, S, $NR^{10}$ or a direct bond; and

Y is O, S or $NR^{11}$; said $R^9$, $R^{10}$ and $R^{11}$ each independently are hydrogen or $C_{1-6}$alkyl; and said $R^{12}$ is hydrogen, $C_{1-6}$alkyl, aryl, $C_{3-6}$cycloalkyl, aryl$C_{1-6}$alkyl, $C_{3-6}$cycloalkyl-$C_{1-6}$alkyl, $C_{3-6}$alkenyl, $C_{3-6}$alkynyl, hydroxy$C_{1-6}$alkyl, $C_{1-6}$alkyloxy$C_{1-6}$alkyl, amino-$C_{1-6}$alkyl or mono or di($C_{1-6}$alkyl)amino$C_{1-6}$alkyl, or in the instance where $Z^1$ is a direct bond or $CH_2$, Y is O, and $Z^2$ is a direct bond, $R^{12}$ may also be halo or hydrazino; and aryl is phenyl, being optionally substituted with 1, 2 or 3 substituents each independently selected from halo, $C_{1-6}$alkyl, trifluoromethyl, nitro, amino, $C_{1-6}$alkyloxy, hydroxy and $C_{1-6}$alkyloxycarbonyl; provided that $R^6$ is other than hydrogen, halo, $C_{1-6}$alkyl, trifluoromethyl, nitro, amino, $C_{1-6}$alkyloxy, hydroxy or $C_{1-6}$alkyloxycarbonyl when X is a direct bond.

A subgroup among the compounds of formula (I) comprises those compounds of formula (I) wherein G is a bivalent radical having a formula (a-1), (a-2), (a-3), (a-4) or (a-5), a particular subgroup thereof comprises those compounds of formula (I) wherein G is a bivalent radical of formula (a-1) or (a-5).

Another subgroup among the compounds of formula (I) comprises those compounds of formula (I) wherein G is a bivalent radical having a formula (a-6) or (a-7).

Among the compounds of the aforementioned subgroups special emphasis is put on those compounds of formula (I) wherein $R^1$ is hydrogen, $C_{1-6}$alkyl, halo, hydroxy, trifluoromethyl, cyano, $C_{1-6}$alkyloxy, $C_{1-6}$alkylthio, $C_{1-6}$alkylsulfinyl, $C_{1-6}$alkylsulfonyl, $C_{1-6}$alkyloxycarbonyl, $C_{1-6}$alkylcarbonyl or aryl; and/or $R^2$ and $R^3$ each independently are hydrogen or $C_{1-4}$alkyl; and/or $R^7$ is hydrogen, $C_{1-4}$alkyl or arylmethyl; and/or X is O, S or NH; and/or $R^4$ and $R^5$ each independently are hydrogen, $C_{1-4}$alkyl, halo, $C_{1-4}$alkyloxy or trifluoromethyl; and/or $R^6$ is hydrogen, $C_{1-4}$alkyl, halo, cyano, nitro, $C_{1-4}$alkyloxy, hydroxy, $C_{1-4}$alkylthio, mercapto, trifluoromethyl, aryl, 4,5-dihydro-2-oxazolyl or 5,6-dihydro-4H-1,3-oxazinyl both radicals being optionally substituted with one or two $C_{1-4}$alkyl substituents, or $R^6$ is a radical of formula $-Z^1-C(Y)-Z^2-R^{12}$ wherein either $Z^1$ is a direct bond, Y is O and $Z^2$ is O or $NR^{10}$, or
$Z^1$ is a direct bond, Y is O and $Z^2$ is a direct bond, or
$Z^1$ is $CH_2$, Y is O and $Z^2$ is O or $NR^{10}$, or
$Z^1$ is $CH_2$, Y is O and $Z^2$ is a direct bond, or
$Z^1$ is O, Y is O, $Z^2$ is a direct bond, or
$Z^1$ is NH, Y is O and $Z^2$ is O, or
$Z^1$ is O, Y is O and $Z^2$ is $NR^{10}$.

A preferred group of compounds of formula (I) comprises those compounds of the aforementioned groups wherein X is O; and/or Alk is a $C_{1-4}$alkanediyl radical; and/or $R^4$ and $R^5$ each independently are hydrogen, $C_{1-4}$alkyl or halo; and/or $R^6$ is halo, cyano, nitro, $C_{1-4}$alkyloxy, aryl, 4,5-dihydro-2-oxazolyl or 5,6-dihydro-4H-1,3-oxazinyl both optionally substituted with one or two $C_{1-4}$alkyl radicals, or $R^6$ is a radical of formula $-Z^1-C(Y)-Z^2-R^{12}$ wherein $Z^1$ is a direct bond, Y is O and $Z^2$ is O or $NR^{10}$.

Particularly preferred compounds within the invention are those preferred compounds wherein $R^1$ is hydrogen, $C_{1-4}$alkyl, halo, hydroxy or $C_{1-4}$alkyloxy; and $R^6$ is a radical of formula $-Z^1-C(Y)-Z-R^{12}$ wherein $Z^1$ is a direct bond, Y is O, $Z^2$ is O and $R^{12}$ is $C_{1-4}$alkyl, aryl$C_{1-4}$alkyl, $C_{3-6}$cycloalkyl$C_{1-4}$alkyl, $C_{3-6}$alkenyl, $C_{3-6}$alkynyl or $C_{1-4}$alkyloxy$C_{1-4}$alkyl.

Especially preferred compounds within the invention are those particularly preferred compounds wherein $R^6$ is $C_{1-4}$alkyloxycarbonyl, particularly ethoxycarbonyl.

Most preferred compounds within the invention are selected from ethyl 4-[2-[1-(6-methyl-3-pyridazinyl)-4-piperidinyl]ethoxy]benzoate, the pharmaceutically acceptable acid-addition salts and possible stereochemically isomeric forms thereof.

As used in the foregoing definitions the term "halo" is generic to fluoro, chloro, bromo and iodo; the term "$C_{1-6}$alkyl" is meant to include straight and branch chained saturated hydrocarbon radicals, having from 1 to 6 carbon atoms such as, for example, methyl, ethyl, propyl, 1-methylethyl, butyl, 1,1-dimethylethyl, pentyl, hexyl and the like; the term "$C_{3-6}$cycloalkyl" is generic to cyclopropyl, cyclobutyl, cyclopentyl and cyclohexyl; the term "$C_{3-6}$alkenyl" defines straight and branch chained hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{3-6}$alkynyl" defines straight and branch chained hydrocarbon radicals containing one triple bond and having from 3 to 6 carbon atoms such as, propargyl, 2-butynyl, 3-butynyl, 2-pentynyl, 3-pentynyl or 4-pentynyl, and when a $C_{3-6}$alkenyl or $C_{3-6}$alkynyl is substituted on a heteroatom, then the carbon atom of said $C_{3-6}$alkenyl or $C_{3-6}$alkynyl connected to said heteroatom preferably is saturated. "$C_{1-6}$alkanediyl" is meant to include a bivalent straight or branch chained hydrocarbon radical having from 1 to 6 carbon atoms; "$C_{2-4}$alkanediyl" is meant to include a bivalent straight or branch chained hydrocarbon radical having from 2 to 4 carbon atoms. Further it should be noted that the left handside nitrogen atom in the bivalent radicals (a-1) through (a-7) is connected to the pyridazine moiety.

The said acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure. Pure isomeric forms of the compounds of formula (I) can be separated from the mixture by conventional separation methods. Preferably, if a specific stereoisomer is desired, said compound will be synthesized by stereoselective methods of preparation. These methods will advantageously employ enantiomerically pure starting materials.

The compounds of formula (I) wherein $R^1$ is hydroxy, mercapto or amino radical may contain in their structure a keto-enol tautomeric system, and consequently the compounds may be present in their keto form as well as their enol form. These tautomeric forms of the compounds of formula (I) are naturally intended to be embraced within the scope of the invention.

The compounds of formula (I) can generally be prepared by reacting an amine of formula (II) with a pyridazine of formula (III) following art-known N-alkylation procedures.

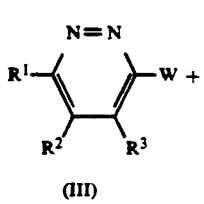

(III)

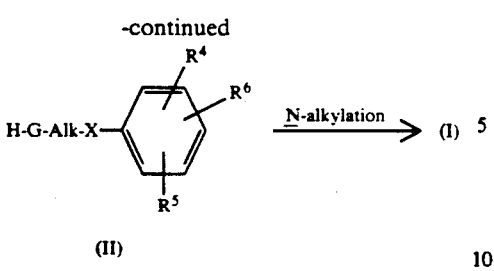

(II)

In formula (III) W represents an appropriate reactive leaving group such as, for example, halo, e.g. fluoro, chloro, bromo, iodo, or a sulfonyloxy group, e.g. 4-methyl-benzenesulfonyloxy, benzenesulfonyloxy, 2-naphthalenesulfonyloxy, methanesulfonyloxy, trifluoromethanesulfonyloxy and the like reactive leaving groups. The N-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethylacetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo-[2.2.2]octane, pyridine and the like, may optionally be used to pick up the acid which is formed during the course of the reaction. In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation reaction under an inert atmosphere such as, for example, oxygen-free argon or nitrogen gas.

Alternatively, said N-alkylation reaction may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reactions products may be isolated from the reaction mixture and, if necessary, further purified according to methodologies generally known in the art such as, for example, extraction, distillation, crystallization, trituration and chromatography.

The compounds of formula (I) wherein X is other than a direct bond, said X being represented by $X^1$ and said compounds by (I-b), can also be prepared by alkylating a phenol, thiophenol or aniline of formula (V) with a pyridazine derivative of formula (IV).

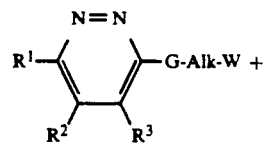

(IV)

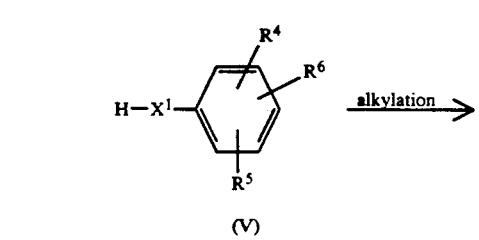

(V)

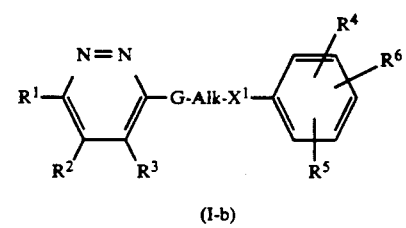

(I-b)

In (IV) W has the previously defined meaning.

Said alkylation reaction can conveniently be carried out by mixing the reactants, optionally in a reaction-inert solvent such as, for example, water; an aromatic solvent, e.g. benzene, methylbenzene, dimethylbenzene and the like; a $C_{1-6}$alkanol, e.g. methanol, ethanol and the like; a ketone, e.g. 2-propanone, 4-methyl-2-pentanone and the like; an ester, e.g. ethylacetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine and the like, may optionally be used to pick up the acid which is formed during the course of the reaction. Further, it may be advantageous to convert the intermediate of formula (V) first into a suitable salt form thereof such as, for example, an alkali or earth alkaline metal salt, by reacting (V) with an appropriate base as defined hereinabove and subsequently using said salt form in the reaction with the alkylating reagent of formula (IV). In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said alkylation reaction under an inert atmosphere such as, for example, oxygen-free argon or nitrogen gas. Said alkylation may also be carried out by applying art-known conditions of phase transfer catalysis reactions as described hereinbefore.

The compounds of formula (I) wherein X is oxygen or sulfur, said X being represented by $X^2$ and said compounds by (I-b-1) can alternatively be prepared by reacting a phenol or thiophenol of formula (VII) with an alcohol of formula (VI) in the presence of a mixture of diethyl azodicarboxylate and triphenylphosphine.

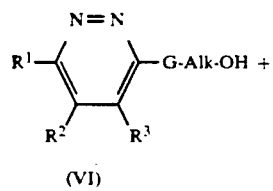

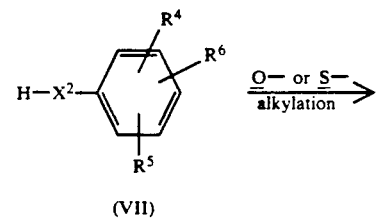

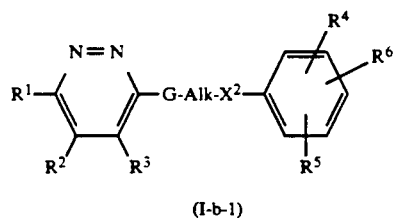

The reaction of (VI) with (VII) can conveniently be conducted in an anhydrous reaction-inert solvent preferably under mild neutral conditions at room temperature or below. A suitable reaction-inert solvent is, for example, an aliphatic hydrocarbon, e.g. hexane and the like, an ether, e.g. 1,1'-oxybisethane, 2,2'-oxybispropane, tetrahydrofuran, 1,4-dioxyane and the like, a dipolar solvent, e.g. hexamethylphosphoric triamide, N,N-dimethylformamide and the like, or a mixture of such solvents.

The compounds of formula (I-b) may also be prepared by reacting an alcohol, thiol or amine of formula (VIII) with an appropriate reagent of formula (IX) according to the hereinbefore described alkylation procedures or the preparation of (I-b) from (IV) and (V).

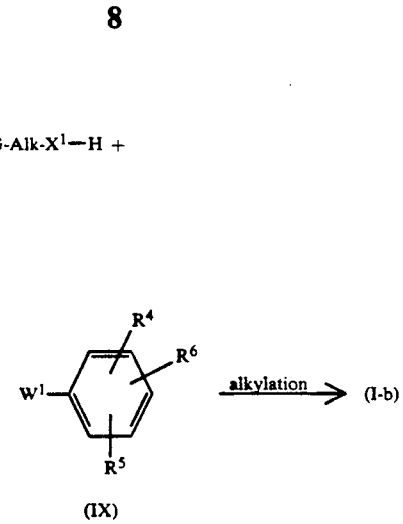

In (VIII) $X^1$ has the hereinbefore described meanings and $W^1$ is a suitable reactive leaving group such as halo, preferably fluoro, chloro or bromo, or nitro.

The compounds of formula (I) wherein G is a bivalent radical of formula (a-5) or (a-7), said bivalent radical being represented by formula $G^1$, and said compounds by (I-c), can also be prepared by N-alkylating an amine of formula (X) with a reagent of formula (XI) following the same procedures as described hereinabove for the preparation of (I) starting from (II) and (III).

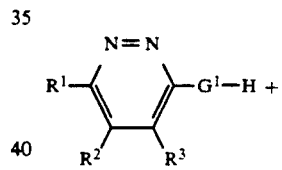

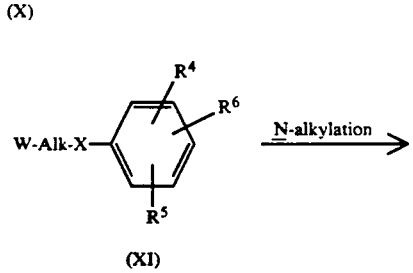

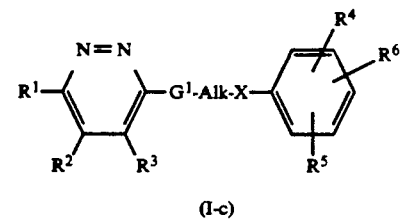

In (XI) W has the previously defined meaning.

The compounds of formula (I-c) can also be prepared by reductively N-alkylating an intermediate of formula (X) with a ketone or aldehyde of formula (XII) following art-known N-alkylation procedures.

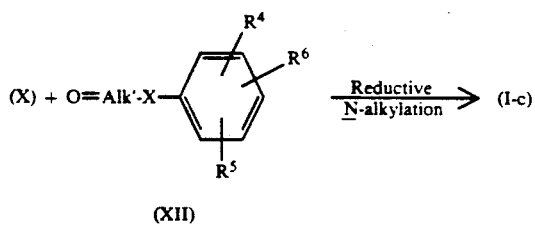

(XII)

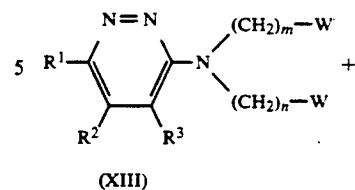

(XIII)

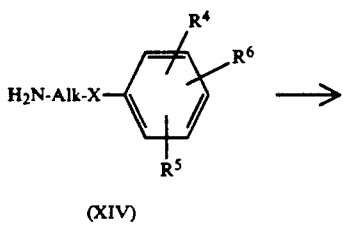

(XIV)

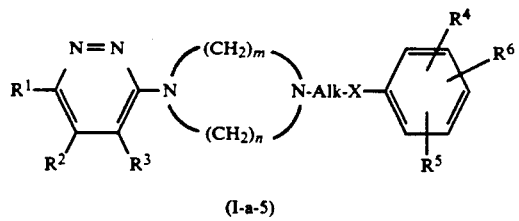

(I-a-5)

In formula (XII) O=Alk'—represents a radical of formula H-Alk—wherein two geminal hydrogen atoms are replaced by oxygen.

Said reductive N-alkylation reaction may conveniently be carried out by reducing a mixture of the reactants in a suitable reaction-inert solvent. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethylacetate, γ-butyrolactone and the like; ethers, e.g. 1,4-dioxane, tetrahydrofuran, 1,1'-oxybisethane, 2-methoxyethanol and the like; halogenated hydrocarbons, e.g. dichloromethane, trichloromethane and the like; dipolar aprotic solvents, e.g. N,N-dimethylformamide, dimethyl sulfoxide and the like; carboxylic acids, e.g. acetic acid, propanoic acid and the like; or a mixture of such solvents. The term "art-known reductive N-alkylation procedures" means that the reaction is carried out either with sodium cyanoborohydride, sodium borohydride, formic acid or a salt thereof, e.g. ammoniumformate and the like reducing agents, or alternatively under a hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

Additionally the compounds of formula (I) wherein G is a bivalent radical of formula (a-5), said compounds being represented by formula (I-a-5), may be prepared by cyclizing an intermediate of formula (XIII) with an amine of formula (XIV).

In (XIII) W has the same meaning as defined hereinabove. The reaction is carried out by stirring the reactants in an appropriate organic solvent such as, for example, 2-propanol, cyclohexanol, 2-propanone and the like, optionally in admixture with an appropriate polar solvent preferably at an elevated temperature. Addition to the reaction mixture of an appropriate base, such as, for example, an alkali or an earth alkaline metal carbonate or hydrogen carbonate or an organic base such as, for example, a tertiary amine, e.g. N,N-diethylethanamine may be suited to pick up the acid which is liberated during the course of the reaction. In order to enhance the rate of the reaction a small amount of an appropriate iodide salt, e.g. sodium or potassium iodide may be added as a reaction promotor.

Compounds of formula (I) wherein G is a bivalent radical of formula (a-1), said compounds being represented by formula (I-a-1), may also be prepared by reacting a ketone (XV) with a phosphonium ylid of formula (XVII) or by reacting an aldehyde (XVI) with a phosphonium ylid of formula (XVIII) following art-known Wittig reaction procedures and subsequently reducing the thus prepared unsaturated intermediates (XIX) and (XX) by an appropriate reduction procedure such as, for example by stirring and, if desired, heating the unsaturated intermediates in a suitable reaction-inert solvent in the presence of hydrogen and an appropriate catalyst such as, for example, palladium-on-charcoal and the like catalysts.

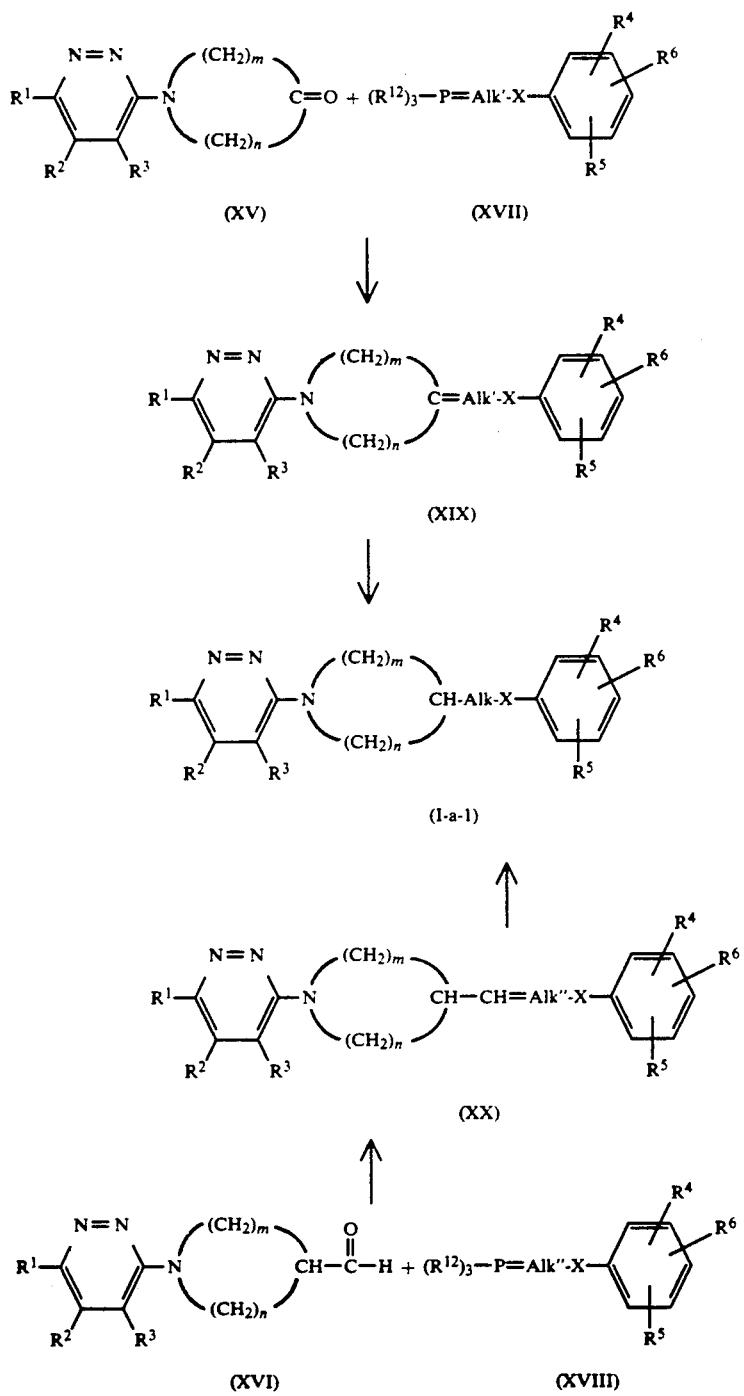

The intermediate phosphonium ylids of formulae (XVII) and (XVIII) may be generated in situ by the reaction of the corresponding alkyl halides with a trialkyl- or triarylphosphine, $(R^{12})_3P$, to yield a phosphonium salt which is converted to the desired phosphonium ylid by abstraction of a proton from it by a strong base such as, for example, methyllithium, butyllithium, sodium amide, sodium hydride, sodium alkoxide and the like bases.

In (XVII) $(R^{12})_3P=Alk'$—represents a radical of formula H-Alk—wherein two geminal hydrogen atoms are replaced by $(R^{12})_3P=$, and $R^{12}$ represents a $C_{1-6}$alkyl or an aryl radical.

In (XVIII) Alk" has the same meaning as Alk' with the proviso that one methylene is missing.

Compounds of formula (I) wherein G is a bivalent radical of formula (a-2), said compounds being represented by (I-a-2), may be prepared by reacting a ketone of formula (XV) with an appropriate organometallic reagent, e.g. an organolithium, an organocopper lithium or an organomagnesium reagent, which is preferably prepared in situ by reaction of an intermediate of formula (XXI) with a suitable metal or metal complex (Metal) according to art-known procedures such as, for example, Grignard procedures.

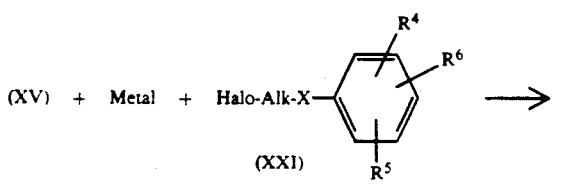

(XV) + Metal + Halo-Alk-X-(XXI) →

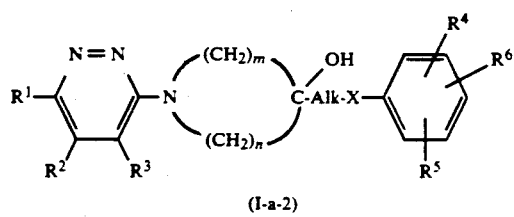

(I-a-2)

Particular compounds of formula (I-a-2) wherein X is oxygen, sulfur or $NR^8$ and Alk is $CH_2$ can also be prepared by reacting an appropriate epoxide of formula (XXII) with a phenol, thiophenol or aniline of formula (XXIII).

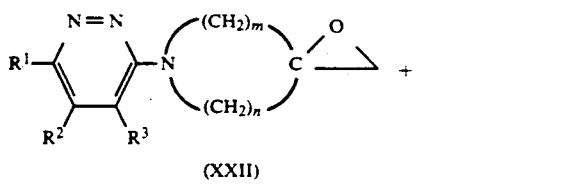

(XXII)

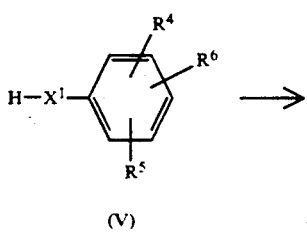

(V)

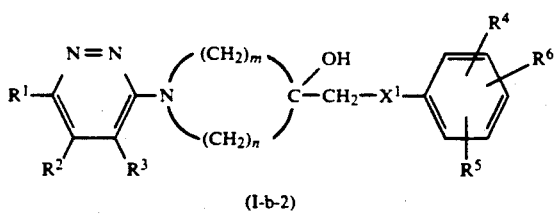

(I-b-2)

The reaction of (XXII) with (V) may be conducted by stirring and, if desired, heating the reactants. The said reaction may be conducted in a suitable solvent such as, for example, a ketone, e.g. 2-propanone, an ether, e.g. tetrahydrofuran, a polar aprotic solvent, e.g. N,N-dimethylformamide and the like solvents.

The compounds of formula (I) can also be converted into each other following art-known functional group transformation procedures.

The compounds of formula (I) wherein $R^1$ is halo may be converted into compounds of formula (I) wherein $R^1$ is hydrogen following art-known hydrogenolysis procedures, i.e. by stirring and, if desired, heating the starting compounds in a suitable reaction-inert solvent in the presence of hydrogen and an appropriate catalyst such as, for example, palladium-on-charcoal and the like catalysts. Said halo atoms may also be replaced by a $C_{1-6}$alkyloxy, aryloxy, aryl$C_{1-6}$alkyloxy, $C_{1-6}$alkylthio or arylthio substituent by reacting the starting compound with an appropriate alcohol or thioalcohol or, preferably an alkali metal or earth alkaline metal salt of said alcohol or thioalcohol, optionally in the presence of an appropriate catalyst such as, for example, a copper salt. Or, said halo atoms may be replaced by a hydroxy substituent by treatment with an alkanoic acid e.g. acetic acid and subsequent hydrolysis by an aqueous hydrohalic solution. In addition, said halo compounds may also be converted into the corresponding mercapto containing compounds by reacting the former with hydrogen sulfide, sodium hydrogen sulfide, sodium sulfide or a reagent capable of generating hydrogen sulfide, e.g. thiourea in the presence of a base.

The compounds of formula (I) wherein $R^1$ is hydroxy may be converted into compounds of formula (I) wherein $R^1$ is halo by treatment with an halogenating agent such as, for example, thionyl chloride, pentachlorophosphorane, sulfuryl chloride and the like. Or, said hydroxy substituent may be converted into a $C_{1-6}$alkyloxy, aryloxy or aryl$C_{1-6}$alkyloxy substituent by O-alkylating the starting compound with an appropriate alkyl halogenide or aryl halogenide in a suitable reaction-inert solvent.

The compounds of formula (I) wherein $R^1$ is arylmethoxy may be converted into the compounds wherein $R^1$ is hydroxy following art-known catalytic hydrogenolysis procedures.

The compounds of formula (I) wherein G is a bivalent radical of formula (a-2) can be converted into the corresponding compounds of formula (I) wherein G is a radical of formula (a-3) by reacting the former compounds with an appropriate deshydrating agent such as, for example, phosphoryl chloride, thionyl chloride and phosphor trichloride, preferably in a suitable solvent such as ethyl acetate, pyridine, N,N-dimethylformamide and the like solvents. Or, the starting hydroxy containing compounds can be treated with a suitable acidic solution preferably at higher temperatures. Suitable acidic solutions contain one or more acids such as sulfuric, hydrochloric, acetic and the like acids in admixture with water and/or an organic solvent, such as methanol, ethanol and the like.

The compounds of formula (I) wherein G is a bivalent radical of formula (a-2) or (a-3) may also be converted into the corresponding compounds wherein G is a bivalent radical of formula (a-1) by an appropriate reduction procedure, e.g. by stirring and, if desired, heating the starting compounds in a suitable reaction-inert solvent in the presence of hydrogen and an appropriate nobel catalyst.

The compounds wherein $R^6$ is cyano may partially or completely be hydrolysed thus yielding compounds of formula (I) wherein the radical $R^6$ is a carboxyl or an aminocarbonyl group. Said partial hydrolysis reaction is preferably conducted in an aqueous acidic medium, e.g. an aqueous sulfuric, hydrochloric or phosphoric acid solution, at room temperature or at a slightly increased temperature. Complete hydrolysis can be accomplished by increasing either the reaction temperature or the reaction time or both. In said complete hydrolysis reaction it may be advantageous to add a second acid to the reaction mixture, e.g. acetic acid.

The compounds of formula (I) wherein the radical $R^6$ is a carboxyl group may be converted into the corresponding acyl halides by treatment with a suitable halogenating agent such as, for example, thionyl chloride, pentachlorophosphorane and sulfuryl chloride.

The thus obtained acyl halides and their corresponding acids can further be derivatized to the corresponding esters or amides by reacting the starting acids or acyl halides with a suitable alkanol or amine following art-known esterification- or amidation reaction procedures. Said reactions are most conveniently conducted in an appropriate solvent such as, for example, tetrahydrofuran, dichloromethane, trichloromethane, acetonitrile and the like solvents. Or, said acids and acyl halides can be converted to their corresponding alkyl or aryl ketones by reacting the acid or acyl halide with an appropriate metal alkyl or metalaryl, e.g. lithiumalkyl, lithiumbenzene, or complex metal alkyl or aryl in a suitable solvent, e.g. tetrahydrofuran.

The compounds of formula (I) wherein the radical $R^6$ is an ester group may be converted into the corresponding carboxylic acid following art-known saponification procedures, e.g. by treating the starting compound with an aqueous alkaline or an aqueous acidic solution.

The compounds wherein $R^6$ is cyano may also be converted into compounds of formula (I) wherein the radical $R^6$ is an imino ester by stirring the nitrile with an alkanol in the presence of a strong acid.

Compounds of formula (I) wherein $R^6$ is a substituted or unsubstituted 4,5-dihydro-2-oxazolyl or 5,6-dihydro-4H-1,3-oxazinyl radical can be prepared by similar procedures as described in the EP-A-207,454 and the EP-A-137,242. For example an appropriate acid, acyl halide or alkyl ester can be condensed with a substituted or unsubstituted hydroxyalkylamine to give a hydroxyalkylamide. The latter may in situ or, if desired, after isolating and purifying it, be cyclized by stirring with thionyl chloride or phosphorous trichloride optionally in the presence of a suitable inert solvent such as, an ether, e.g. tetrahydrofuran, 1,4-dioxane and the like, a halogenated hydrocarbon, e.g. trichloromethane, dichloromethane, an ester, e.g. ethyl acetate, isopropyl acetate and the like solvents.

A number of intermediates and starting materials in the foregoing preparations are known compounds which may be prepared according to art-known methodologies of preparing said or similar compounds and some intermediates are new. A number of such preparation methods will be described hereinafter in more detail.

Intermediates of formula (II) wherein X is other than a direct bond, said X being represented by $X^1$, and said intermediates by (II-b) can be prepared by alkylating an alcohol, thioalcohol or amine of formula (V) with a reagent of formula (XXIII), following the alkylation reaction procedures described hereinbefore for the preparation of (I-b) from (IV) and (V), and subsequently removing the protective group P in the thus obtained intermediate (XXIV) following art-known procedures, e.g. by hydrolysis in an acidic or an alkaline aqueous medium or by catalytic hydrogenation depending upon the nature of P.

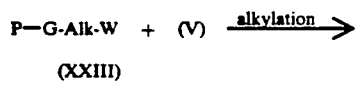

(XXIII)

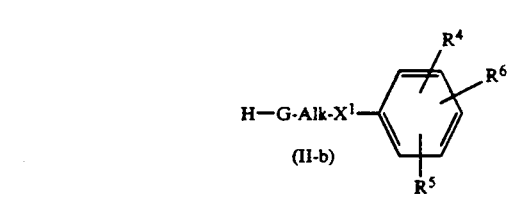

In the reaction of (XXIII) with (V) and in the following reaction schemes P represents a suitable protective group which readily removeable by hydrogenation or hydrolysation. Preferred protective groups may be, for example, hydrogenolyzable groups e.g. phenylmethyl and the like, and hydrolyzable groups e.g. $C_{1-6}$alkylcarbonyl and the like.

Alternatively compounds of formula (II-b) wherein $X^1$ is oxygen or sulfur may also be prepared by reacting P-G-Alk-OH, (XXV) with an thiol or alcohol of formula (VII) according to similar procedures as described hereinbefore for the synthesis of (I-b-1) starting from (VI) and (VII), and subsequently removing the protective group P in the thus obtained intermediate.

In addition, intermediates of formula (II) wherein G is a bivalent radical of formula (a-5) or (a-7), said bivalent radical being represented by $G^1$ and said intermediates by (II-c) may also be prepared by N-alkylating an amine of formula (XXVI) with a reagent of formula (XI), following N-alkylation procedures described hereinbefore, and subsequently removing the protective group P in the thus obtained intermediate (XXVII).

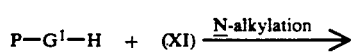

(XXVI)

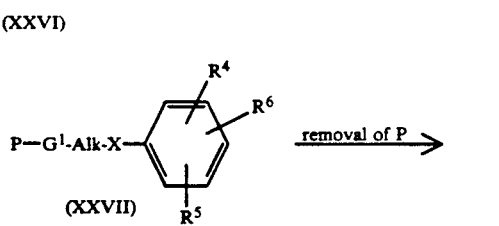

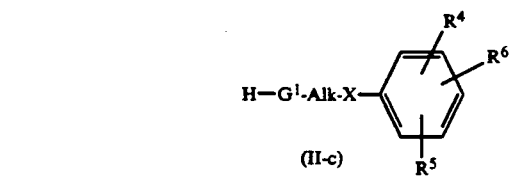

Intermediates of formula (IV) can be prepared by N-alkylating a pyridazine of formula (III) with an amine of formula H-G-Alk-OH, (XXVIII), following art-known N-alkylation procedures and subsequently converting the alcohol function of the thus obtained intermediate (VI) into an appropriate leaving group with an appropriate halogenating agent such as, for example, thionyl chloride, sulfuryl chloride, pentachlorophosphorane, pentabromophosphorane or an appropriate sulfonyl halide such as, for example, methanesulfonyl chloride or 4-methylbenzenesulfonyl chloride.

Intermediates of formula (XXVIII) may be derived from a carboxylic acid, P-G-Alk'''—C(O)—OH, (XXIX) or the corresponding ester or acyl halide thereof by reduction with an appropriate reductant e.g. a borane-methyl sulfide complex, sodium borohydride, lithium aluminum hydride and the like, following art-known reduction procedures and removing the protective group P in the thus obtained alcohol. Alk''' in (XXIX) has the same meaning as Alk provided that one methylene function is missing.

Starting materials and intermediates used in all of the preceding procedures for which no specific preparation is given herein, are generally known, may be prepared according similar procedures as described hereinbefore for compounds of formula (I), and/or may be prepared following art-known methodologies described in the literature for the preparation of similar known compounds. For example, intermediates of formula (X) may be prepared according to similar procedures as described in the EP-A-156,433, published Oct. 2, 1985 which corresponds to U.S. Ser. No. 702,772. Whereas intermediates of formula (V) and (XI) wherein $R^6$ is a substituted or unsubstituted 4,5-dihydro-2-oxazolyl or 2-oxazolyl or a substituted or unsubstituted $4\underline{H}$-1,3-oxazinyl or 5,6-dihydro-$4\underline{H}$-1,3-oxazinyl radical may be prepared following similar procedures as described in EP-A-137,242 and EP-A-207,454. All references cited hereinabove are incorporated herein by reference for the processes for preparation.

The compounds of formula (I) and some of the intermediates in this invention may have an asymmetric carbon atom in their structure. This chiral center may be present in a R- and a S-configuration, this R- and S-notation being in correspondence with the rules described in J. Org. Chem., 35, 2849-2867 (1970).

Pure sterochemically isomeric forms of the compounds of this invention may be obtained by the application of art-known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

The compounds of formula (I) and the pharmaceutically acceptable acid addition salts and stereoisomeric forms show antiviral activity and are particularly attractive due to their favourable therapeutic index, resulting from an acceptable low degree of cell toxicity, combined with a desirable antiviral activity at very low doses.

The antiviral properties of the compounds of formula (I) can be demonstrated for example in the "Picornavirus Minimal Inhibitory Concentration (MIC)"-test illustrating the useful antiviral activity of the compounds of the present invention.

The compounds of the present invention are therefore useful agents in combating viruses. The compounds of formula (I), the pharmaceutically acceptable acid addition salts and stereochemically isomeric forms thereof are particularly active against a broad spectrum of picornaviruses, including enteroviruses e.g. Poliovirus type 1,2 and 3, Coxsackieviruses, Echoviruses, Enteroviruses, e.g. Enterovirus 70 and especially numerous strains of rhinoviruses, e.g. Human Rhinovirus serotypes HRV -2, -3, -4, -5, -6, -9, -14, -15, -29, -39, -41, -51, -59, -63, -70, -72, -85, -86, -89 and the like.

In view of their potent, local as well as systemic, antiviral activity the compounds of this invention constitute useful tools for the destruction and prevention of the growth of viruses and more particularly there is provided a method of treating viral diseases in warm-blooded animals suffering from said viral diseases, especially respiratory diseases e.g. common cold, pneumonia, bronchiolitis, herpangina and the like, CNS-diseases e.g. paralysis, aseptic meningitis, encephalitis and the like, cardiac disease e.g. pericarditis, myocarditis and the like, hepatic diseases e.g. hepatitis and the like, gastrointestinal diseases e.g. diarrhea and the like, ophtalmic diseases e.g. acute hemorrhagic conjunctivitis and the like, dermatological diseases e.g. exanthem, rash, hand-foot-and-mouth disease, and the like diseases. Said method comprises the systemic or topical administration to warm-blooded animals of an antivirally effective amount of a least one compound of formula (I), a pharmaceutically acceptable acid addition salt or stereoisomeric form thereof.

The subject compounds may be formulated into various pharmaceutical forms for systemic or topical administration purposes. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, intranasally, by parenteral injection or for ophtalimic administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions can take the form of creams, lotions, aerosols and/or emulsions and can be included in a trasdermal patch of the matrix or reservoir type as are conventional in the art for this purpose.

In the compositions suitable for topical administration the active ingredient will preferably be a semisolid such as a thickened composition such as salves, creams, gellies, ointments and the like which can be applied by a swab. Pharmaceutical composition suitable for topical administration may also be in form of drops, lotions or an aerosol. Suitable aerosol preparations may include solutions and solids in powder form, which may be in combination with a pharmaceutically acceptable carrier, such as an inert compressed gas. Acid addition salts of (I) due to their increased water solubility over the corresponding base form, are obviously more suitable in the preparation of aqueous compositions.

In a further aspect of the invention there are provided particular pharmaceutical compositions which comprise a compound of formula (I), a pharmaceutically acceptable acid addition salt or a stereochemically isomeric form thereof and a cyclodextrin or a derivative thereof. When applied to the site of infection such cyclodextrin based compositions result in a continuous and controlled delivery of sufficiently high concentrations of the antiviral compound of formula (I) to the site of the infection for sustained periods of time.

Said compositions are particularly convenient for treating local viral infections, in particular mucosal infections, e.g. nasal or eye infections.

The cyclodextrin to be used in the aforementioned compositions include the pharmaceutically acceptable unsubstituted and substituted cyclodextrins known in the art, more particularly $\alpha,\beta$ or $\gamma$ cyclodextrins or the pharmaceutically acceptable derivatives thereof.

Substituted cyclodextrins which can be used in the invention include polyethers described in U.S. Pat. No. 3,459,731 which is incorporated by reference for the definition and processes for preparation. In general, unsubstituted cyclodextrins are reacted with an alkylene oxide, preferably under superatmospheric pressure and at an elevated temperature, in the presence of an alkaline catalyst.

Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy$C_{1-6}$alkyl, carboxy$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

In the foregoing definitions the term "$C_{1-6}$alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.125 to 3, in particular 0.3 to 2, more in particular 0.3 to 1 and the MS is in the range of 0.125 to 10, in particular of 0.3 to 3 and more in particular 0.3 to 1.5.

Other references describing cyclodextrins for use in the compositions according to the present invention, and which provide a guide for the preparation and characteristics of cyclodextrins, for the process of depositing the selected agent within the cyclodextrin molecule of the use of cyclodextrins in pharmaceutical compositions include the following:

"Cyclodextrin Chemistry" by M. L. Bender et al., Springer-Verlag, Berlin (1978); Advances in Carbohydrate Chemistry", Vol. 12 Ed. by M. L. Wolfrom, Academic Press, New York (157) in the chapter *The Schardinger Dextrins* by Dexter French at p. 189-260; "Cyclodextrins and their Inclusions Complexes" by J. Szejtli, Akademiai Kiado, Budapest, Hungary (1982); I. Tabushi in Acc. Chem. Research, 1982, 15, p. 66-72; W. Sanger, Angewandte Chemie, 92, p. 343-361 (1981); A. P. Croft and R. A. Bartsch in Tetrahedron, 39, p. 1417-1474 (1983); German Offenlegungsschrift DE 3118218; German Offenlegungsschrift DE 3317064; EP-A-94,157; EP-A-149,197; U.S. Pat. No. 4,659,696; and U.S. Pat. No. 4,383,992.

Of particular utility in the invention are the $\beta$-cyclodextrin ethers, e.g. dimethyl-$\beta$-cyclodextrin as described in Drugs of the Future, Vol. 9, No. 8, p. 577-578 by M. Nogradi (1984) and polyethers, e.g. hydroxypropyl $\beta$-cyclodextrin and hydroxyethyl $\beta$-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between $\beta$-cyclodextrin an propylene oxide and may have a MS value of about 0.125 to 10, e.g. about 0.3 to 3.

In the invention, the molecules of the antiviral compounds of formula (I) are surrounded, at least in part, by the cyclodextrin, i.e. the agent fits into the cyclodextrin cavity.

To prepare said particular cyclodextrin based pharmaceutical compositions of the invention, the selected antiviral compound (or compounds) of formula (I), the pharmaceutically acceptable acid addition salt of the stereochemically isomeric form thereof is deposited within the cyclodextrin molecule itself, such process being known in the art for other active agents. In the final compositions, the molar ratio of cyclodextrin:antiviral compound is from about 1:1 to about 5:1, in particular, about 1:1 to about 2:1. Thus, in general, the composition will be prepared by dissolving the cyclodextrin in water and adding the antiviral compound to this solution, preferably under vigorous stirring and preferably at a temperature in the range of 10° C. to 50° C., in particular in range of 15° C. to 30° C., and preferably at room temperature.

In the final compositions, the cyclodextrin will comprise about 2.5 to 40% by weight, in particular about 2.5 to 25%, more in particular 5 to 20%, for example about 10%, with the remainder being water, preservative, the active ingredient and any excipients.

In particular, the pharmaceutical compositions may consist only of water, cyclodextrin and the antiviral agents without the need for co-solvents such as ethanol or surfactants.

Application of the cyclodextrin based compositions of the invention may be by aerosol, e.g. with a propellant such as nitrogen, carbon dioxide, a freon, or without a propellant such as a pump spray, drops, or a semisolid such as a thickened compositions which can be applied by a swab. In particular applications, semisolid compositions such as salves, creams, gellies, ointments and the like will conveniently be used.

For the liquid preparations of said cyclodextrin based compositions, any of the usual pharmaceutical media may be added, such as, for example, glycols, oils, alcohols and the like, however in concentrations below the level of irritation. In order to stabilize the formulations the pH may be increased or decreased or stabilized by adding appropriate acids, bases or buffer systems, e.g. citrate, phosphate buffers. Further additives may comprise substances to make the formulations isotonical, e.g. sodium chloride, mannitol, glucose and the like. It is further recommendable to add a preservative to the formulations such as, for example, a mercury salt or complex salt, e.g. phenyl mercuriacetate, nitrate, chloride or borate, phenylethyl alcohol, ethanol, propylene glycol and the like. Suitable thickeners for obtaining the above-mentioned thickened compositions comprise polyvinyl alcohols, hydroxypropyl methyl celluloses, hydroxyethyl celluloses, methylcelluloses, polyvinyl pyrrolidone, acrylic acid polymers and the like.

Depending on the type of virus which is to be controlled, said cyclodextrin based compositions can be applied in the vagina, nose, mouth, eyes, lungs or within the cheeks so as to control viruses which have not entered the blood stream of the patient, e.g. viruses which are located in mucous membranes of the body. The cyclodextrin based compositions of the invention are particularly useful on those infection sites where the natural defense mechanisms prevent the delivery of antiviral agents during sustained periods due to an effective elimination of the active compound from the site of infection. Such elimination may be due to clearance by ciliary movement of secretion, or by absorption.

As part of the pharmaceutical composition, one may also include the same or a different active antiviral in a different delivery carrier so as to provide a different profile of activity, e.g. a wide range of time during which the composition shows activity or a supplement to bolster a low level at a particular point in the release schedule of the cyclodextrin.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, drops, teaspoonfuls, tablespoonfuls and the like, and segregated multiples thereof.

Those of skill in treating antiviral diseases in warm-blooded animals could easily determine the effective amount from the test results presented hereinafter. In general it is contemplated that an effective amount would be from 0.001 mg/kg to 50 mg/kg body weight, preferably from 0.01 mg/kg to 10 mg/kg body weight.

The following examples are intended to illustrate and not to limit the scope of the present invention in all its aspects. Unless otherwise stated all parts therein are by weight.

EXPERIMENTAL PART

A. Preparation of Intermediates

EXAMPLE 1 a) To a stirred and cooled (0° C.) mixture of 4.5 parts of 2-amino-2-methyl-1-propanol and 130 parts of dichloromethane were added portionwise 4.93 parts of 4-(phenylmethoxy)benzoyl chloride. Upon complete addition, stirring was continued for 48 hours at room temperature. The precipitate was filtered off and the filtrate was evaporated. The residue was stirred in 2,2'-oxybispropane. The precipitated product was filtered off and stirred in 9.6 parts of thionyl chloride during 1 hour. After evaporation, the residue was taken up in a sodium hydroxide solution 10%, crushed ice and methylbenzene. The separated organic layer was washed with water, dried, filtered and evaporated, yielding 5 parts (90%) of 4,5-dihydro-4,4-dimethyl-2-[4-(phenylmethoxy)phenyl]oxazole as a residue (int. 1).

b) A mixture of 5 parts of 4,5-dihydro-4,4-dimethyl-2-[4-(phenylmethoxy)phenyl]oxazole and 80 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 2 parts (100%) of 4-(4,5-dihydro-4,4-dimethyl-2-oxazolyl)phenyl as a residue (int. 2).

EXAMPLE 2 a) A mixture of 12.8 parts of ethyl 4-(phenylmethoxy)benzoate, 180 parts of benzene and 5 drops of a sodium methoxide solution 30% was stirred and refluxed using a water separator. 10.8 Parts of cyclopropanemethanol in 90 parts of benzene was added dropwise during a period of 1 hour. Upon complete addition, stirring was continued for 4 hours at reflux. After cooling, the whole was washed with water, the organic layer was dried, filtered and evaporated, yielding 14 parts (100%) of (cyclopropylmethyl) 4-(phenylmethoxy)benzoate as a residue (int. 3).

b) A mixture of 14 parts of (cyclopropylmethyl) 4-(phenylmethoxy)benzoate and 200 parts of 2-propanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 8.1 parts (100%) of (cyclopropylmethyl) 4-hydroxybenzoate as a residue (int. 4).

EXAMPLE 3

To a stirred mixture of 0.5 parts of N,N,N-triethylbenzenemethanaminium chloride, 4 parts of sodium hydroxide and 40 parts of water were added dropwise 16 parts of 2-chloro-4-methoxyphenol and 18.2 parts of 1,2-dibromoethane at 50° C. Upon complete addition, stirring was continued overnight at 50° C. The reaction mixture was poured into water and the product was extracted with a mixture of 2,2′-oxybispropane and dichloromethane. The extract was dried, filtered and evaporated, yielding 14 parts (52.7%) of 1-(2-bromoethoxy)-2-chloro-4-methoxybenzene as a residue (int. 5).

In a similar manner there were also prepared:
2-chloro-1-(3-chloropropoxy)-4-methoxybenzene (int. 6);
2-[4-(3-chloropropoxy)phenyl]-4,5-dihydro-4,4-dimethyloxazole (int. 7);
2-[4-(2-chloroethoxy)phenyl]-4,5-dihydro-4,4-dimethyloxazole (int. 8);
2-[4-(3-chloropropoxy)phenyl]-4,5-dihydrooxazole (int. 9);
1,4-dichloro-2-(3-chloropropoxy)-5-methoxybenzene (int. 10); and
2,3-dichloro-1-(3-chloropropoxy)-4-methoxybenzene (int. 11).

EXAMPLE 4 a) A mixture of 3.16 parts of ethyl 1-piperazinecarboxylate, 4.7 parts of 2-chloro-1-(3-chloropropoxy)-4-methoxybenzene, 3.2 parts of sodium carbonate and 67.5 parts of N,N-dimethylformamide was stirred overnight at reflux temperature. After cooling, the reaction mixture was poured into water and the product was extracted with 2,2′-oxybispropane. The extract was dried, filtered and evaporated. The residue was converted into the hydrochloride salt in 2,2′-oxybispropane. The salt was filtered off and dried, yielding 4 parts (50%) of ethyl 4-[3-(2-chloro-4-methoxyphenoxy)propyl]-1-piperazinecarboxylate monohydrochloride (int. 12).

b) A mixture of 3.56 parts of ethyl 4-[3-(2-chloro-4-methoxyphenoxy)propyl]-1-piperazinecarboxylate monohydrochloride, 3.6 parts of potassium hydroxide and 80 parts of 2-propanol was stirred overnight at reflux temperature. After evaporation, the residue was taken up in water and the product was extracted with dichloromethane. The extract was dried, filtered and evaporated. The residue was converted into the hydrochloride salt in 2-propanol. The salt was filtered off and crystallized from 2-propanol. The product was filtered off and dried, yielding 1.33 parts (37.1%) of 1-[3-(2-chloro-4-methoxyphenoxy)propyl]piperazine dihydrochloride; mp. 190° C. (int. 13).

In a similar manner there was also prepared:
1-[2-(2-chloro-4-methoxyphenoxy)ethyl]piperazine dihydrochloride (int. 14).

EXAMPLE 5 a) A mixture of 47.6 parts of 1-(phenylmethyl)piperazine, 65.8 parts of 2-[4-(3-chloropropoxy)phenyl]-4,5-dihydrooxazole, 28.6 parts of sodium carbonate and 282 parts of N,N-dimethylformamide was stirred over weekend at 60°~65° C. The reaction mixture was evaporated and the residue was taken up in water. The product was extracted with dichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was converted into the (Z)-2-butenedioate salt in methanol. The salt was filtered off, washed with methanol and 2,2′-oxybispropane and crystallized from methanol. The product was filtered off, washed with water and dried at 70° C., yielding 40.6 parts (24.5%) of 1-[3-[4-(4,5-dihydro-2-oxazolyl)phenoxy]propyl]-4-(phenylmethyl)piperazine (Z)-2-butenedioate(1:2); mp. 178.0° C. (int. 15).

b) A mixture of 56 parts of 1-[3-[4-(4,5-dihydro-2-oxazolyl)phenoxy]propyl]-4-(phenylmethyl)piperazine and 480 parts of methanol was hydrogenated at normal pressure and at 50° C. with 5 parts of palladium-on-charcoal catalyst 10%. After the calculated amount of hydrogen was taken up, the catalyst was filtered off and the filtrate was evaporated. The residue was taken up in water and the product was extracted with dichloromethane. The extract was dried, filtered and evaporated, yielding 46.9 parts (100%) of 1-[3-[4-(4,5-dihydro-2-oxazolyl)phenoxy]propyl]piperazine as a residue (int. 16).

In a similar manner there was also prepared:
1-[3-[4-(4,5-dihydro-4,4-dimethyl-2-oxazolyl)phenoxy]propyl]piperazine as a residue (int. 17).

EXAMPLE 6 a) To 180 parts of 1,2-dimethoxyethane were added portionwise 15.1 parts of a sodium hydride dispersion 50%. After cooling in an ice/salt bath, a solution of 70.6 parts of ethyl (diethoxyphosphinyl) acetate in 180 parts of 1,2-dimethoxyethane was added dropwise while stirring vigorously at <5° C. Upon completion, stirring was continued for 30 minutes while cooling and then for 1.5 hour at room temperature. A solution of 51 parts of methyl 3-methyl-4-oxo-1-piperidinecarboxylate in 180 parts of 1,2-dimethoxyethane was added dropwise (ice/salt bath; about 10° C.). Upon complete addition, the mixture was stirred overnight at room temperature. Water was added to the oily layer while stirring vigorously and the whole was extracted twice with 2,2′-oxybispropane. The extract was washed three times with water, dried, filtered and evaporated. The residue was distilled at 6.65 Pa, yielding 56.9 parts (78.6%) of methyl 4-(2-ethoxy-2-oxoethylidene)-3-methyl-1-piperidinecarboxylate; bp. 100° C. (int. 18).

b) A mixture of 56.9 parts of methyl 4-(2-ethoxy-2-oxoethylidene)-3-methyl-1-piperidinecarboxylate and 400 parts of ethanol was hydrogenated at normal pressure and at room temperature with 3 parts of palladium-on-charcoal. After the calculated amount of hydrogen was taken up, the catalyst was filtered off and the filtrate was evaporated, yielding 57 parts (99%) of ethyl cis-1-(methoxycarbonyl)-3-methyl-4-piperidineacetate (int. 19).

In a similar manner there were also prepared:
ethyl cis-3-methoxy-1-(phenylmethyl)-4-piperidineacetate (int. 20);
ethyl 8-(ethoxycarbonyl)-8-azabicyclo[3.2.1]octane-3-acetate (int. 21); and
cis-3-(phenylmethoxy)-1-(phenylmethyl)-4-piperidineethanol (int. 22).

EXAMPLE 7 a) To a stirred mixture of 100 parts of ethyl 1-(phenylmethyl)-3-pyrrolidinecarboxylate and 525 parts of trichloromethane were added dropwise 47 parts of ethyl carbonochloridate at 20° C. (cooling). Upon complete addition, stirring was continued for 1 hour at room temperature, for 2 hours at reflux temperature and then overnight at room temperature. After evaporation, 2,2'-oxybispropane and activated charcoal were added and the whole was filtered over diatomaceous earth. The filtrate was evaporated, yielding 90 parts (98%) of diethyl 1,3-pyrrolidinecarboxylate as an oily residue (int. 23).

b) To a stirred solution of 67.2 parts of potassium hydroxide in 500 parts of water was added dropwise a solution of 90 parts of diethyl 1,3-pyrrolidinecarboxylate in 200 parts of ethanol at ±15° C. Upon completion, stirring was continued overnight at room temperature. Ethanol was distilled off and to the remaining residue was added crushed ice. The whole was acidified with hydrochloric acid and extracted with dichloromethane. The extract was dried, filtered and evaporated, yielding 44 parts (56%) of 1-(ethoxycarbonyl)-3-pyrrolidinecarboxylic acid as an oily residue (int. 24).

c) To a stirred solution of 44 parts of 1-(ethoxycarbonyl)-3-pyrrolidinecarboxylic acid in 520 parts of dichloromethane were added dropwise 35.7 parts of thionyl chloride at 20° C. Upon complete addition, stirring was continued overnight and the reaction mixture was evaporated, yielding 49 parts (100%) of ethyl 3-(chlorocarbonyl)-1-pyrrolidinecarboxylate as an oily residue (int. 25).

d) A mixture of 22 parts of ethyl 3-(chlorocarbonyl)-1-pyrrolidinecarboxylate, 36 parts of N,N-dimethylacetamide, 3 parts of a thiophene solution 4% in methanol and 210 parts of 2,2'-oxybispropane was hydrogenated at normal pressure and at room temperature with 3 parts of palladium-on-charcoal catalyst 10%. After the calculated amount of hydrogen was taken up, the catalyst was filtered off and the filtrate was evaporated, yielding 17 parts (93%) of ethyl 3-formyl-1-pyrrolidinecarboxylate as a residue (int. 26).

e) To a stirred and cooled (ice-water) mixture of 18 parts of ethyl 3-formyl-1-pyrrolidinecarboxylate and 100 parts of pyridine were added first 11.4 parts of 1,3-propanedicarboxylic acid and then 5 drops of piperidine. Upon complete addition, stirring was continued for 3 hours at reflux. The reaction mixture was evaporated, yielding 13 parts (57%) of 3-[1-(ethoxycarbonyl)-3-pyrrolidinyl]-2-propenoic acid as an oily residue (int. 27).

f) A mixture of 13 parts of 3-[1-(ethoxycarbonyl)-3-pyrrolidinyl]-2-propenoic acid and 100 parts of acetic acid was hydrogenated at normal pressure and at 20° C. with 2 parts of palladium-on-charcoal catalyst 10%. After the calculated amount of hydrogen was taken up, the catalyst was filtered off and the filtrate was evaporated. The residue was taken up in methylbenzene and the latter was evaporated again, yielding 13 parts (100%) of 1-(ethoxycarbonyl)-3-pyrrolidinepropanoic acid as a residue (int. 28).

In a similar manner there was also prepared: 1-(ethoxycarbonyl)-4-piperidinebutanoic acid (int. 29).

EXAMPLE 8 a) A sodium ethoxide solution was prepared starting from 400 parts of ethanol and 13 parts of sodium. After removal of the excess of ethanol, 700 parts of 1,1'-oxybisethane and 79 parts of iodomethane were added dropwise to 159 parts of ethyl α-cyano-1-(phenylmethyl)-4-piperidineacetate. Upon complete addition, stirring was continued overnight at room temperature. The precipitate was filtered off and the filtrate was evaporated. The residue was converted into the hydrochloride salt in 2-propanol. The salt was filtered off and dried, yielding 100 parts (53.7%) of ethyl α-cyano-α-methyl-1-(phenylmethyl)-4-piperidineacetate monohydrochloride (int. 30).

b) To 45 parts of cooled ethyl α-cyano-α-methyl-1-(phenylmethyl)-4-piperidineacetate were added 250 parts of a sodium hydroxide solution 2N. After stirring overnight at room temperature, the reaction mixture was cooled, neutralized with hydrochloric acid and then evaporated. The residue was taken up in 45 parts of N,N-dimethylacetamide and the whole was heated for 5 hours at 150° C. and then evaporated again, yielding 16 parts (30.3%) of α-methyl-1-(phenylmethyl)-4-piperidineacetonitrile monohydrochloride (int. 31).

c) 29.2 Parts of α-methyl-1-(phenylmethyl)-4-piperidineacetonitrile monohydrochloride were added portionwise to 166 parts of a sulfuric acid solution 70%. Upon complete addition, stirring was continued for 6 hours at about 150° C. After cooling, 240 parts of ethanol were added and the whole was stirred and refluxed overnight. The reaction mixture was cooled, poured into crushed ice and treated with ammonium hydroxide. The product was extracted with dichloromethane. The extraxt was dried, filtered and evaporated, yielding 22 parts (72.7%) of ethyl α-methyl-1-(phenylmethyl)-4-piperidineacetate (int. 32).

EXAMPLE 9 a) To a stirred and cooled (15° C.) mixture of 11.1 parts of potassium hydroxide and 96 parts of water was added dropwise a solution of 31.8 parts of ethyl 1-[(phenylmethoxy)carbonyl]-4-piperidinepropanoate in 38 parts of ethanol during 20 minutes. Upon complete addition, stirring was continued overnight at room temperature. The reaction mixture was evaporated at <50° C. The reaction mixture was poured into crushed ice and treated with concentrated hydrochloric acid. The separated aqueous layer was extracted with dichloromethane. The extract was dried, filtered and evaporated, yielding 29 parts (100%) of 1-[(phenylmethoxy)carbonyl]-4-piperidinepropanoic acid as a residue (int. 33).

b) To a stirred mixture of 29 parts of 1-[(phenylmethoxy)carbonyl]-4-piperidinepropanoic acid and 520 parts of dichloromethane were added dropwise 14.9 parts of thionyl chloride. Upon complete addition, stirring was continued overnight at room temperature. The reaction mixture was evaporated, yielding 28.3 parts (91.5%) of (phenylmethyl) 4-(3-chloro-3-oxopropyl)-1-piperidinecarboxylate as a residue (int. 34).

c) To a stirred and cooled (ice bath, 10° C.) mixture of 3.4 parts of sodium tetrahydroborate and 188 parts of N,N-dimethylformamide were added dropwise 28 parts of (phenylmethyl) 4-(3-chloro-3-oxopropyl)-1-piperidinecarboxylate (exothermic reaction, the temperature rose to 38° C.). Upon complete addition, the reaction mixture was stirred over weekend at room temperature. The reaction mixture was poured into water and the product was extracted with methylbenzene. The extract was dried, filtered and evaporated, yielding 15.4 parts (61.6%) of (phenylmethyl) 4-(3-hydroxypropyl)-1-pipridinecarboxylate as a residue (int. 35).

In a similar manner there were also prepared:
ethyl 4-(4-hydroxybutyl)-1-piperidinecarboxylate as a residue (int. 36);

ethyl 3-(3-hydroxypropyl)-1-piperidinecarboxylate as an oily residue (int. 37);
ethyl 3-(2-hydroxyethyl)-8-azabicyclo[3.2.1]octane-8-carboxylate as a residue (int. 38); and
ethyl cis-4-(2-hydroxyethyl)-3-methyl-1-piperidinecarboxylate as a residue (int. 39).

EXAMPLE 10

270 Parts of tetrahydrofuran were added carefully to 10 parts of lithium tetrahydroaluminate. A solution of 66 parts of ethyl 1-(phenylmethyl)-4-piperidinepropanoate in 180 parts of tetrahydrofuran was added dropwise to the thus obtained mixture (exothermic reaction, the temperature rose to about 45° C.). The whole was stirred overnight at reflux temperature. The mixture was cooled in an ice salt bath and decomposed at 0° C. with successively 10.5 parts of water, 7.8 parts of a sodium hydroxide solution 20% and 33.8 parts of water. The mixture was filtered over diatomaceous earth and the filtrate was evaporated, yielding 56 parts (100% of 1-(phenylmethyl)-4-piperidinepropanol as a residue (int. 40).

In a similar manner there were also prepared:
cis-3-(phenylmethoxy)-1-(phenylmethyl)-4-piperidineethanol as a residue (int. 41);
cis-3-methoxy-1-(phenylmethyl)-4-piperidineethanol as an oily residue (int. 42); and
β-methyl-1-(phenylmethyl)-4-piperidineethanol as a residue (int. 43).

EXAMPLE 11 a) To a stirred solution of 152 parts of sodium hydroxide in 1000 parts of water was added a solution of 249.5 parts of 4-piperidinepropanoic acid acetate (1:1) in 900 parts of water. 270 Parts of tetrahydrofuran were added. After cooling in a 2-propanone/CO$_2$-bath, a solution of 119.4 parts of ethyl carbonochloridate in 270 parts of tetrahydrofuran was added dropwise. Upon completion, stirring was continued for 3 hours at a temperature between 0°-5° C. The whole was washed twice with 420 parts of 1,1'-oxybisethane. The aqueous phase was acidified with concentrate hydrochloric acid. The product was extracted three times with 520 parts of dichloromethane. The whole was evaporated. The oily residue was suspended five times in 210 parts of petroleumether and the latter was decanted each time. The residue was evaporated to dry, yielding 200 parts (93%) of 1-(ethoxycarbonyl)-4-piperidinepropanoic acid as an oily residue (int. 44).

b) To a stirred mixture of 200 parts of 1-(ethoxycarbonyl)-4-piperidinepropanoic acid and 750 parts of trichloromethane were added 320 parts of thionyl chloride. The whole was stirred for 18 hours at room temperature. The reaction mixture was evaporated with methylbenzene. The residue was distilled, yielding 102.6 parts (47%) of ethyl 4-(3-chloro-3-oxopropyl)-1-piperidinecarboxylate; bp. 165-170 at 399 Pa (int. 45).

c) A mixture of 102 parts of ethyl 4-(3-chloro-3-oxopropyl)-1-piperidinecarboxylate, 45 parts of 2,6-dimethylpyridine and 630 parts of tetrahydrofuran was hydrogenated at normal pressure and at room temperature with 5 parts of palladium-on-charcoal catalyst 10%. After the calculated amount of hydrogen was taken up, the catalyst was filtered off and the filtrate was evaporated. The residue was dissolved in 650 parts of dichloromethane. The solution was washed twice with 100 parts of a hydrochloric acid solution 5% and twice with 100 parts of water, dried, filtered and evaporated. The residue was distilled, yielding 71.1 parts (81%) of ethyl 4-(3-oxopropyl)-1-piperidinecarboxylate; bp. 130°-135° C. at 133 Pa (int. 46).

d) A mixture of 36 parts of ethyl 4-(3-oxopropyl)-1-piperidinecarboxylate and 450 parts of tetrahydrofuran was hydrogenated at normal pressure and at 20° C. with 2 parts of Raney nickel catalyst. After the calculated amount of hydrogen was taken up, the catalyst was filtered off and the filtrate was evaporated. The residue was dissolved in 260 parts of dichloromethane. The organic layer was washed with 100 parts of a diluted hydrochloric acid solution, dried, filtered and evaporated, yielding 36 parts (98.3%) of ethyl 4-(3-hydroxypropyl)-1-piperidinecarboxylate as a residue (int. 47).

In a similar manner there were also prepared:
methyl 3-(2-hydroxyethyl)-1-pyrrolidinecarboxylate as a residue (int. 48); and
ethyl 4-(2-hydroxyethyl)-1-piperidinecarboxylate as a residue (int. 49).

EXAMPLE 12 a) To a stirred and cooled (−10° C.) mixture of 19.6 parts of triphenyl phosphine and 54 parts of tetrahydrofuran were added portionwise 13.7 parts of diethyl diazenedicarboxylate (exothermic reaction). Upon completion, stirring was continued for 15 minutes and then a solution of 16.5 parts of 1-(phenylmethyl)-4-piperidineethanol and 12.5 parts of ethyl 4-hydroxybenzoate in 54 parts of tetrahydrofuran was added dropwise at a temperature between 0° and −5° C. After complete addition, the whole was stirred overnight at room temperature and then evaporated. Water was added to the residue and the product was extracted with dichloromethane. The extract was dried, filtered and evaporated. The residue was dissolved in 2,2'-oxybispropane and allowed to crystallize. The precipitate was filtered off and the filtrate was evaporated. The residue was converted into the (Z)-2-butenedioate salt in 280 parts of 2-propanol. The salt was filtered off and dried, yielding 15 parts (42%) of ethyl 4-[2-[1-(phenylmethyl)-4-piperidinyl]ethoxy]benzoate (Z)-2-butenedioate(1:1); mp. 142.0° C. (int. 50).

b) A mixture of 4.8 parts of ethyl 4-[2-[1-(phenylmethyl)-4-piperidinyl]ethoxy]benzoate (Z)-2-butenedioate(1:1) and 120 parts of ethanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was crystallized from 2-propanol, yielding 4.5 parts (100%) of ethyl 4-[2-(4-piperidinyl)ethoxy]benzoate butanedioate(1:1); mp. 146.7° C. (int. 51).

In a similar manner there were also prepared:
ethyl cis-4-[2-(3-hydroxy-4-piperidinyl)ethoxy]benzoate as a residue (int. 52);
ethyl 4-[2-(4-piperidinyl)ethoxy]benzeneacetate as an oily residue (int. 53);
ethyl 4-[3-(4-piperidinyl)propoxy]benzeneacetate as an oily residue (int. 54);
ethyl cis-4-[2-(3-methoxy-4-piperidinyl)ethoxy]benzoate as an oily residue (int. 55);
ethyl 4-[2-[3-(phenylmethoxy)-4-piperidinyl]ethoxy]benzoate as a residue (int. 56); and
ethyl 4-[2-(4-piperidinyl)propoxy]benzoate as a residue (int. 57).

EXAMPLE 13 a) To a stirred mixture of 36 parts of ethyl 4-(3-hydroxypropyl)-1-piperidinecarboxylate and 261 parts of benzene were added dropwise 21.5 parts of thionyl chloride at 5°-10° C. Upon complete addition, stirring was continued overnight at this temperature. The reaction mixture was evaporated and the residue was taken up in methylbenzene. The solvent was evaporated (this was repeated twice), yielding 33 parts (83.8%) of ethyl 4-(3-chloropropyl)-1-piperidinecarboxylate as a residue (int. 58).

b) A mixture of 15 parts of 4-(5,6-dihydro-4H-1,3-oxazin-2-yl)phenol hydrochloride, 29 parts of potassium carbonate and 180 parts of N,N-dimethylformamide was stirred for 1 hour at about 80° C. Then there were added 16.4 parts of ethyl 4-(3-chloropropyl)-1-piperidinecarboxylate and stirring was continued overnight at about 95° C. The reaction mixture was poured into ice water and the product was extracted with dichloromethane. The extract was dried, filtered and evaporated. The residue was purified by column chromatography over silica gel using a mixture of trichloromethane and methanol (98.5:1.5 by volume) as eluent. The pure fractions were collected and the eluent was evaporated, yielding 18.8 parts (71.7%) of ethyl 4-[3-[4-(5,6-dihydro-4H-1,3-oxazin-2-yl)phenoxy]propyl]-1-piperidinecarboxylate; mp. 128.5° C. (int. 59).

c) A mixture of ethyl 4-[3-[4-(5,6-dihydro-4H-1,3-oxazin-2-yl)phenoxy]propyl]-1-piperidinecarboxylate, 26.3 parts of potassium hydroxide and 200 parts of 2-propanol was stirred and refluxed for 3 hours. After evaporation, water was added and the solvent was distilled off till all traces of 2-propanol were removed. After cooling, ice water was added and the product was extracted with dichloromethane. The organic layer was dried, filtered and evaporated, yielding 14.5 parts (100%) of 5,6-dihydro-2-[4-[3-(4-piperidinyl)propoxy]phenyl]-4H-1,3-oxazine as a residue (int. 60).

In a similar manner there were also prepared:
4-[3-[4-(4,5-dihydro-2-oxazolyl)phenoxy]propyl]piperidine as a residue (int. 61);
4-[[4-(4,5-dihydro-4,4-dimethyl-2-oxazolyl)phenoxy]methyl]piperidine as a residue (int. 62);
4,5-dihydro-4,4-dimethyl-2-[4-[2-(3-pyrrolidinyl)ethoxy]phenyl]oxazole as a residue (int. 63);
4-[3-[2,6-dichloro-4-(4,5-dihydro-2-oxazolyl)phenoxy]propyl]piperidine as a residue (int. 64);
ethyl 4-[3-(4-piperidinyl)propoxy]benzoate as a residue (int. 65);
4-[4-[4-(4,5-dihydro-2-oxazolyl)phenoxy]butyl]piperidine as a residue (int. 66);
4-[3-[2-chloro-4-(4,5-dihydro-2-oxazolyl)phenoxy]propyl]piperidine as a residue (int. 67);
4,5-dihydro-4,4-dimethyl-2-[4-[3-(3-pyrrolidinyl)propoxy]phenyl]oxazole as a residue (int. 68);
4-[3-(2,3-dichloro-4-methoxyphenoxy)propyl]piperidine as a residue (int. 69);
4-[3-(2,5-dichloro-4-methoxyphenoxy)propyl]piperidine as a residue (int. 70); and
cis-4-[2-[4-(4,5-dihydro-2-oxazolyl)phenoxy]ethyl]-3-methylpiperidine as a residue (int. 71).

EXAMPLE 14 a) To a stirred mixture of 56 parts of 1-(phenylmethyl)-4-piperidinepropanol, 40 parts of N,N-diethylethanamine and 600 parts of trichloromethane were added dropwise 34.5 parts of methanesulfonyl chloride at 15° C. After cooling, stirring was continued overnight at room temperature. Water was added to the mixture and the layers were separated. The organic layer was dried, filtered and evaporated, yielding 60 parts (72.5%) of 1-(phenylmethyl)-4-piperidinepropanol methanesulfonate(ester) as a residue (int. 72).

b) 4.8 Parts of a sodium hydride dispersion 50% were washed with petroleum ether under nitrogen atmosphere to remove the oil. After drying under nitrogen, 135 parts of N,N-dimethylformamide were added. 15.5 Parts of 4-(4,5-dihydro-4,4-dimethyl-2-oxazolyl)phenol were added portionwise and upon completion, stirring was continued for 1.5 hours at room temperature. A solution of 26.5 parts of 1-(phenylmethyl)-4-piperidinepropanol methanesulfonate(ester) in 18 parts of N,N-dimethylformamide was added dropwise. Upon complete addition, stirring was continued overnight at room temperature. The reaction mixture was evaporated and the residue was taken up in water. The oil was extracted with dichloromethane. The extract was dried, filtered and evaporated, yielding 13.5 parts (40.9%) of 4-[3-[4-(4,5-dihydro-4,4-dimethyl-2-oxazolyl)phenoxy]propyl]-1-(phenylmethyl)piperidine as a residue (int. 73).

c) A mixture of 13.5 parts of 4-[3-[4-(4,5-dihydro-4,4-dimethyl-2-oxazolyl)phenoxy]propyl]-1-(phenylmethyl)piperidine and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 9.5 parts (90.9%) of 4-[3-[4-(4,5-dihydro-4,4-dimethyl-2-oxazolyl)phenoxy]propyl]piperidine as a residue (int. 74).

d) A mixture of 5 parts of 4-[2-[4-(4,5-dihydro-4,4-dimethyl-2-oxazolyl)phenoxy]ethyl]-1-(phenylmethyl)piperidine and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 3.4 parts (86.4%) of 4-[2-[4-(4,5-dihydro-4,4-dimethyl-2-oxazolyl)phenoxy]ethyl]piperidine as a residue (int. 75).

EXAMPLE 15 a) A mixture of 7.4 parts of ethyl 4-formyl-1-piperidinecarboxylate, 6.5 parts of 4-(4,5-dihydro-2-oxazolyl)benzamine (described in C.A. 32, P 47267), 2 parts of a solution of thiophene in methanol 4% and 160 parts of methanol was hydrogenate at normal pressure and at room temperature with 2 parts of palladium-on-charcoal catalyst 10%. After the calculated amount of hydrogen was taken up, the catalyst was filtered off over diatomaceous earth and the filtrate was evaporated. The residue was dried, yielding 16.2 parts (100%) of ethyl 4-[[[4-(4,5-dihydro-2-oxazolyl)phenyl]amino]methyl]-1-piperidinecarboxylate as a residue (int. 76).

b) A mixture of 13.3 parts of ethyl 4-[[[4-(4,5-dihydro-2-oxazolyl)phenyl]amino]methyl]-1-piperidinecarboxylate, 22.4 parts of potassium hydroxide and 240 parts of 2-propanol was stirred for 6 hours at reflux temperature. The reaction mixture was evaporated. The residue was taken up in water and the whole was evaporated again till all traces of 2-propanol were removed. The product was extracted with dichloromethane. The extract was dried, filtered and evaporated. The residue was purified by column chromatography over silica gel using a mixture of trichloromethane and methanol (97:3 by volume) as eluent. The pure fractions were collected and the eluent was evaporated, yielding 5.1 parts (49.1%) of N-[4-(4,5-dihydro-2-oxazolyl)phenyl]-4-piperidinemethanamine as a residue (int. 77).

EXAMPLE 16 a) A mixture of 37.5 parts of 6-(phenylmethyl)-1-oxa-6-azaspiro[2.5]octane, 24.9 parts of ethyl 4-hydroxybenzoate, 20.7 parts of potassium carbonate and 200 parts of 4-methyl-2-pentanone was stirred overnight at reflux temperature. After cooling, water was added. The precipitated product was filtered off, washed with water and crystallized from 1,1'-oxybisethane. The product was filtered off and dried, yielding 23 parts (41.5%) of ethyl 4-[[4-hydroxy-1-(phenylmethyl)-4-piperidinyl]methoxy]benzoate; mp. 100.2° C. (int. 78).

b) A mixture of 23 parts of ethyl 4-[[4-hydroxy-1-(phenylmethyl)-4-piperidinyl]methoxy]benzoate and 200 parts of ethanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 17 parts (100%) of ethyl 4-[(4-hydroxy-4-piperidinyl)methoxy]benzoate as a residue (int. 79).

EXAMPLE 17 a) A mixture of 10.7 parts of methyl 4-[[4-hydroxy-1-(phenylmethyl)-4-piperidinyl]methoxy]benzoate and 8 parts of 2-aminoethanol was stirred for 4 hours in an oil bath at 145° C. After cooling, the reaction mixture was poured into water. The oil was decanted, washed twice with water and the product was extracted with dichloromethane. The extract was dried, filtered and evaporated. The residue was crystallized from a mixture of 2,2'-oxybispropane and 2-propanol. The product was filtered off and dried, yielding 8 parts (69.3%) of N-(2-hydroxyethyl)-4-[[4-hydroxy-1-(phenylmethyl)-4-piperidinyl]methoxy]benzamide; mp. 161.1° C. (int. 80).

b) A mixture of 23 parts of N-(2-hydroxyethyl)-4-[[4-hydroxy-1-(phenylmethyl)-4-piperidinyl]methoxy]benzamide and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 16 parts (90.5%) of N-(2-hydroxyethyl)-4-[(4-hydroxy-4-piperidinyl)methoxy]benzamide as an oily residue (int. 81).

In a similar manner there was also prepared:
N-(2-hydroxyethyl)-4-[2-(4-piperidinyl)ethoxy]benzamide as a residue (int. 82).

EXAMPLE 18 a) A mixture of 19.3 parts of 3-chloro-6-methylpyridazine, 19.4 parts of 4-piperidineethanol, 16 parts of sodium carbonate and 0.9 parts of N,N-dimethylacetamide was stirred for 5 hours at about 150° C. After cooling, the reaction mixture was diluted with water and the product was extracted twice with dichloromethane. The combined extracts were washed with water, dried, filtered and evaporated, yielding 31.5 parts (95%) of 1-(6-methyl-3-pyridazinyl)-4-piperidineethanol (int. 83).

b) To a stirred and cooled (ice bath) solution of 7.1 parts of thionyl chloride in 65 parts of dichloromethane was added dropwise a solution of 6.6 parts of 1-(6-methyl-3-pyridazinyl)-4-piperidineethanol in 195 parts of dichloromethane. Upon complete addition, stirring was continued overnight at room temperature. The reaction mixture was washed with alkaline water. The separated organic layer was dried, filtered and evaporated, yielding 7.2 parts (100%) of 3-[4-(2-chloroethyl)-1-piperidinyl]-6-methylpyridazine as a residue (int. 84).

In a similar manner there were also prepared:
3-chloro-6-[4-(3-chloropropyl)-1-piperidinyl]pyridazine as a residue (int. 85);
3-chloro-6-[4-(2-chloroethyl)-1-piperidinyl]pyridazine as a residue (int. 86);
3-chloro-6-[4-(chloromethyl)-1-piperidinyl]pyridazine as a residue (int. 87);
3-chloro-6-[3-(chloromethyl)-1-pyrrolidinemethanol as a residue (int. 88);
3-chloro-6-[4-(4-chlorobutyl)-1-piperidinyl]pyridazine as a residue (int. 89);
3-chloro-6-[3-(2-chloroethyl)-1-piperidinyl]pyridazine as a residue (int. 90);
3-(2-chloroethyl)-8-(6-chloro-3-pyridazinyl)-8-azabicyclo[3.2.1]octane as a residue (int. 91);
3-[4-(3-chloropropyl)-1-piperidinyl]-6-methylpyridazine as a residue (int. 92); and
3-[4-(chloromethyl)-1-piperidinyl]-6-methylpyridazine as a residue (int. 93).

EXAMPLE 19

A mixture of 8.9 parts of 3,6-dichloropyridazine, 8.6 parts of 3-(2-chloroethyl)pyrrolidine hydrochloride, 21.2 parts of sodium carbonate and 235 parts of N,N-dimethylformamide was stirred overnight at about 65° C. The reaction mixture was poured into ice water and the product was extracted with dichloromethane. The extract was dried, filtered and evaporated, yielding 12.2 parts (99.1%) of 3-chloro-6-[3-(2-chloroethyl)-1-pyrrolidinyl]pyridazine as a residue (int. 94).

EXAMPLE 20 a) 5.7 Parts of sodium (in pieces) were added to 86 parts of methanol. After the dropwise addition of 12.1 parts of 1-(6-chloro-3-pyridazinyl)-4-piperidineethanol, the reaction mixture was stirred overnight at reflux temperature. After cooling, the whole was poured into ice water and the product was extracted with dichloromethane. The extract was dried, filtered and evaporated. The residue was purified by column chromatography over silica gel using a mixture of methylbenzene and methanol (90:10 by volume) as eluent. The desired fraction was collected and the eluent was evaporated, yielding 7.3 parts (61.5%) of 1-(6-methoxy-3-pyridazinyl)-4-piperidineethanol as a residue (int. 95).

b) A solution of 7.3 parts of 1-(6-methoxy-3-pyridazinyl)-4-piperidineethanol in 130 parts of dichloromethane was added dropwise to 7.3 parts of thionyl chloride at room temperature. Upon complete addition, stirring was continued overnight at room temperature. The residue was taken up in water and the product was extracted with dichloromethane. The extract was dried, filtered and evaporated, yielding a first fraction of 1.8 parts of 3-[4-(2-chloroethyl)-1-piperidinyl]-6-methoxypyridazine. The aqueous layer was neturalized with an ammonium hydroxide solution. The precipitated product was filtered off and taken up in dichloromethane. The organic layer was dried, filtered and evaporated, yielding a second fraction of 4.0 parts of 3-[4-(2-chloroethyl)-1-piperidinyl]-6-methoxypyridazine. Total yield: 5.8 parts (73.4%) of 3-[4-(2-chloroethyl)-1-piperidinyl]-6-methoxypyridazine as a residue (int. 96).

In a similar manner there were also prepared:

3-[4-(3-chloropropyl)-1-piperidinyl]-6-methoxypyridazine monohydrochloride as a residue (int. 97); and
3-[4-(chloromethyl)-1-piperidinyl]-6-methoxypyridazine monohydrochloride as a residue (int. 98).

EXAMPLE 21 a) A mixture of 6 parts of 1-(6-chloro-3-pyridazinyl)-4-piperidinepropanol, 1.9 parts of sodium acetate and 150 parts of acetic acid was stirred for 4 hours at reflux temperature. The reaction mixture was evaporated and the residue was taken up in 200 parts of a hydrochloric acid solution 10%. After stirring for 1 hour at reflux temperature, the whole was evaporated. The residue was taken up in water and treated with ammonium hydroxide. The product was extracted with dichloromethane. The extract was dried, filtered and evaporated, yielding a first fraction of 6-[4-(3-hydroxypropyl)-1-piperidinyl]-3(2H)-pyridazinone;

From the remaining aqueous layer, the precipitated product was filtered off and crystallized from 2-propanol. The product was filtered off and dried at 60° C., yielding a second fraction of the desired intermediate.

Total yield: 1.6 parts (29.3%) of 6-[4-(3-hydroxypropyl)-1-piperidinyl]-3(2H)-pyridazinone; mp. 173.8° C. (int. 99).

b) To a stirred and cooled (ice bath) mixture of 2.8 parts of 6-[4-(3-hydroxypropyl)-1-piperidinyl]-3(2H)-pyridazinone, 65 parts of dichloromethane and 45 parts of tetrahydrofuran were added dropwise 2.8 parts of thionyl chloride. Upon complete addition, stirring was continued overnight at room temperature. The whole was evaporated and the residue was taken up in methylbenzene. The organic layer was evaporated again, yielding 3 parts (100%) of 6-[4-(3-chloropropyl)-1-piperidinyl]-3(2H)-pyridazinone as a residue (int. 100).

In a similar manner there was also prepared:
6-[4-(2-chloroethyl)-1-piperidinyl]-3(2H)-pyridazinone as a residue (int. 101).

EXAMPLE 22

A mixture of 14.9 parts of 3,6-dichloropyridazine, 30 parts of 1,2-ethanediamine and 218 parts of methylbenzene was stirred for 5 hours at reflux temperature. After cooling, water was added and the layers were separated. The aqueous layer was evaporated. The residue was stirred for 3 hours in 225 parts of tetrahydrofuran. The whole was filtered and the filtrate was evaporated. The residue was converted into the (E)-2-butenedioate salt in 2-propanol. The salt was filtered off and dried, yielding 3 parts (61.9%) of N-(6-chloro-3-pyridazinyl)-1,2-ethanediamine (E)-2-butenedioate (2:1); mp. 210° C. (int. 102).

In a similar manner there were also prepared: 1-(6-chloro-3-pyridazinyl)hexahydro-1H-1,4-diazepine monohydrochloride (int. 103); and
3-chloro-6-(3-methyl-1-piperazinyl)pyridazine; mp. 78.6° C. (int. 104).

EXAMPLE 23 a) A mixture of 70 parts of 3-(trifluoromethyl)benzenamine hydrochloride, 26.5 parts of 2-propenenitrile and 36.5 parts of N-ethylethanamine was stirred for 2.5 hours at 180° C. After cooling to 0° C., the whole was treated with a sodium hydroxide solution. The product was extracted with dichloromethane. The extract was washed with water, dried, filtered and evaporated, yielding 34.5 parts (45%) of 3-[[3-(trifluoromethyl)phenyl]amino]propanenitrile as a residue (int. 105).

b) A mixture of 13.6 parts of 3-[[3-(trifluoromethyl)phenyl]amino]propanenitrile and 400 parts of methanol saturated with ammonia was hydrogenated at normal pressure and at a temperature below 20° C. with 3 parts of Raney Nickel catalyst. After the calculated amount of hydrogen was taken up, the catalyst was filtered off and the filtrate was evaporated, yielding 13 parts (100%) of $N^1$-[3-(trifluoromethyl)phenyl]-1,3-propanediamine as a residue (int. 106).

EXAMPLE 24 a) A mixture of 6-bromohexanenitrile, 12 parts of 4-(2-oxazolyl)phenol monohydrochloride, 16.6 parts of potassium carbonate and 282 parts of N,N-dimethylformamide was stirred overnight at 60° C. After cooling, the reaction mixture was poured into water and the product was extracted with methylbenzene. The extract was washed with water, dried, filtered and evaporated. The residue was crystallized from 2,2'-oxybispropane. The product was filtered off and dried, yielding 3.2 parts (20.6%) of 6-[4-(4,5-dihydro-2-oxazolyl)phenoxy]hexanenitrile (int. 107).

b) A mixture of 3.2 parts of 6-[4-(4,5-dihydro-2-oxazolyl)phenoxy]hexanenitrile and 80 parts of methanol, saturated with ammonia, was hydrogenated at normal pressure and at room temperature with 1 part of Raney-nickel catalyst. After the calculated amount of hydrogen was taken up, the catalyst was filtered off and the filtrate was evaporated, yielding 3.2 parts (100%) of 6-[4-(4,5-dihydro-2-oxazolyl)phenoxy]hexanamine as a residue (int. 108).

B. Preparation of the Final Compounds

EXAMPLE 25

A mixture of 10.4 parts of 3-chloro-6-methylpyridazine, 22.4 parts of ethyl 4-[2-(4-piperidinyl)ethoxy]benzoate butanedioate (1:1), 8.6 parts of sodium carbonate and 0.9 parts of N,N-dimethylformamide was stirred for 3 hours in an oil bath at ±150° C. After cooling, water and dichloromethane were added and the layers were separated. The organic layer was dried, filtered and evaporated. The residue was purified by column chromatography over silica gel using a mixture of trichloromethane and ethanol (99:1 by volume) as eluent. The pure fractions were collected and the eluent was evaporated. The residue was crystallized from a mixture of 2,2'-oxybispropane and 2-propanone (75:25 by volume). The precipitated product was filtered off and dried, yielding 17 parts (56.8%) of ethyl 4-[2-[1-(6-methyl-3-pyridazinyl)-4-piperidinyl]ethoxy]benzoate; mp. 130.1° C. (comp. 1).

In a similar manner there were also prepared:

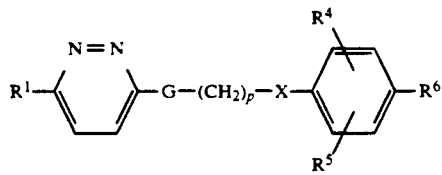

| Comp. No. | R¹ | G | p | X | R⁴ | R⁵ | R⁶ | mp. (°C.)/salt |
|---|---|---|---|---|---|---|---|---|
| 2 | Cl— | —NH— | 3 | —NH— | 3-CH₃ | —H | —H | 127.0 |
| 3 | Cl— | —NH— | 3 | —NH— | 3-Cl | —H | —H | 115.0 |
| 4 | Cl— | 4-hydroxy-4-methylpiperidin-1-yl | 1 | —O— | —H | —H | —H | 154.6 |
| 5 | Cl— | —NH— | 3 | —NH— | 3-CF₃ | —H | —H | 156.6 2(COOH)₂ |
| 6 | Cl— | piperidin-1,4-diyl | 3 | —O— | —H | —H | 4,4-dimethyl-2-oxazolin-2-yl | 159.2 |
| 7 | Cl— | piperazin-1,4-diyl | 2 | —O— | 2-Cl | —H | —OCH₃ | 125.5 |
| 8 | Cl— | piperazin-1,4-diyl | 3 | —O— | 2-Cl | —H | —OCH₃ | 109.5 |
| 9 | Cl— | piperazin-1,4-diyl | 3 | —O— | —H | —H | 4,4-dimethyl-2-oxazolin-2-yl | 155.9 |
| 10 | Cl— | piperidin-1,4-diyl | 2 | —O— | —H | —H | 4,4-dimethyl-2-oxazolin-2-yl | 124.5 |
| 11 | Cl— | piperidin-1,4-diyl | 3 | —O— | —H | —H | 2-oxazolin-2-yl | 172.8 |
| 12 | Cl— | piperidin-1,4-diyl | 1 | —O— | —H | —H | 4,4-dimethyl-2-oxazolin-2-yl | 199.2 |
| 13 | —COOCH₃ | piperazin-1,4-diyl | 3 | —O— | —H | —H | 2-oxazolin-2-yl | 196.1 |
| 14 | —SO₂—CH₃ | piperazin-1,4-diyl | 3 | —O— | —H | —H | 2-oxazolin-2-yl | 197.9 |

-continued

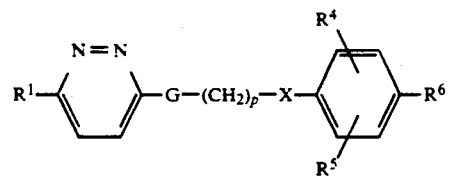

| Comp. No. | R¹ | G | p | X | R⁴ | R⁵ | R⁶ | mp. (°C.)/salt |
|---|---|---|---|---|---|---|---|---|
| 15 | Cl— | —N⟨piperidine⟩ | 2 | —O— | —H | —H | oxazoline with gem-diCH₃ | 160.6 |
| 16 | —SO—CH₃ | —N⟨piperazine⟩N— | 3 | —O— | —H | —H | oxazoline | 188.2 |
| 17 | —CN | —N⟨piperazine⟩N— | 3 | —O— | —H | —H | oxazoline | 189.1 |
| 18 | —CH₃ | —N⟨piperazine⟩N— | 3 | —O— | —H | —H | oxazoline | 157.1 |
| 19 | Cl— | —N⟨piperidine⟩ | 1 | —NH— | —H | —H | oxazoline | 201.1 |
| 20 | Cl— | —N⟨piperidine⟩ | 1 | —O— | —H | —H | —CONH(CH₂)₂OH | — |
| 21 | Cl— | —N⟨piperidine⟩ | 3 | —O— | 2-Cl | 6-Cl | oxazoline | 136.4 H₂O/* |
| 22 | 4F—C₆H₅— | —N⟨piperazine⟩N— | 3 | —O— | —H | —H | oxazoline | 249.9 |
| 23 | Cl— | —N⟨piperidine⟩ | 3 | —O— | —H | —H | —COOC₂H₅ | 117.5 |
| 24 | Cl— | —N⟨piperidine⟩ | 4 | —O— | —H | —H | oxazoline | 174.5 |
| 25 | Cl— | —N⟨piperidine⟩ | 3 | —O— | 2-Cl | —H | oxazoline | 170.5 |
| 26 | Cl— | —N⟨piperidine⟩ | 3 | —O— | —H | —H | 6-membered oxazine | 183.7 |

-continued

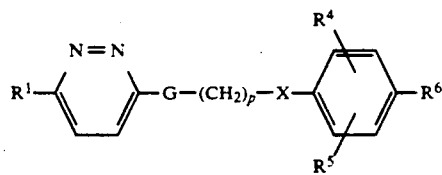

| Comp. No. | R¹ | G | p | X | R⁴ | R⁵ | R⁶ | mp. (°C.)/salt |
|---|---|---|---|---|---|---|---|---|
| 27 | Cl— | -N⟨pyrrolidine⟩- | 3 | —O— | —H | —H | oxazoline with gem-diCH₃ | 141.7 |
| 28 | Cl— | —NH— | 6 | —O— | —H | —H | oxazoline | 154.7 |
| 29 | Cl— | -N⟨piperidine⟩- | 3 | —O— | 2-Cl | 3-Cl | —OCH₃ | 159.2 |
| 30 | Cl— | -N⟨piperidine⟩- | 3 | —O— | 2-Cl | 5-Cl | —OCH₃ | 131.3 |
| 31 | —COOC₂H₅ | -N⟨piperidine⟩- | 2 | —O— | —H | —H | —COOC₂H₅ | 134.8 |
| 32 | —CN | -N⟨piperidine⟩- | 2 | —O— | —H | —H | —COOC₂H₅ | 144.7 |
| 33 | —SO₂—CH₃ | -N⟨piperidine⟩- | 2 | —O— | —H | —H | —COOC₂H₅ | 155.5 |
| 34 | —S—CH₃ | -N⟨piperidine⟩- | 2 | —O— | —H | —H | —COOC₂H₅ | 102.4 |
| 35 | —SO—CH₃ | -N⟨piperidine⟩- | 2 | —O— | —H | —H | —COOC₂H₅ | 99.1 |
| 36 | Cl— | -N⟨3-CH₃-piperidine⟩- | 2 | —O— | —H | —H | oxazoline | 101.6/* |
| 37 | Cl— | -N⟨piperidine⟩- | 2 | —O | —H | —H | —CONHC₂H₄OH | 160.4 |

-continued

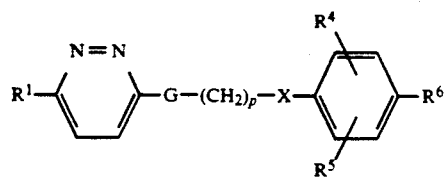

| Comp. No. | $R^1$ | G | p | X | $R^4$ | $R^5$ | $R^6$ | mp. (°C.)/salt |
|---|---|---|---|---|---|---|---|---|
| 38 | $-CH_3$ | -N(4-methylpiperidine) | 3 | $-O-$ | $-H$ | $-H$ | $-COOC_2H_5$ | 114.1 |
| 39 | $Cl-$ | -N(3-OH, 4-methylpiperidine) | 2 | $-O-$ | $-H$ | $-H$ | $-COOC_2H_5$ | 154.3/cis |
| 40 | $-SO-CH_3$ | -N(4-methylpiperidine) | 3 | $-O-$ | $-H$ | $-H$ | $-COOC_2H_5$ | 89.5 |
| 41 | $Cl-$ | -N(4-methylpiperidine) | 2 | $-O-$ | $-H$ | $-H$ | $-CH_2COOC_2H_5$ | 79.1 |
| 42 | $-S-CH_3$ | -N(4-methylpiperidine) | 3 | $-O-$ | $-H$ | $-H$ | $-COOC_2H_5$ | 103.8 |
| 43 | $Cl-$ | -N(4-methylpiperidine) | 3 | $-O-$ | $-H$ | $-H$ | $-CH_2COOC_2H_5$ | 79.1 |
| 44 | $Cl-$ | -N(3-OCH$_3$, 4-methylpiperidine) | 2 | $-O-$ | $-H$ | $-H$ | $-COOC_2H_5$ | 141.9/cis |
| 45 | $-CN$ | -N(4-methylpiperidine) | 3 | $-O-$ | $-H$ | $-H$ | $-COOC_2H_5$ | 154.4 |
| 46 | $-COOC_2H_5$ | -N(4-methylpiperidine) | 3 | $-O-$ | $-H$ | $-H$ | $-COOC_2H_5$ | 117.2 |
| 47 | $-SO_2-CH_3$ | -N(4-methylpiperidine) | 3 | $-O-$ | $-H$ | $-H$ | $-COOC_2H_5$ | 130.9 |
| 48 | $Cl-$ | -N(3-OCH$_2$-C$_6$H$_5$, 4-methylpiperidine) | 2 | $-O-$ | $-H$ | $-H$ | $-COOC_2H_5$ | 112.9 |

-continued

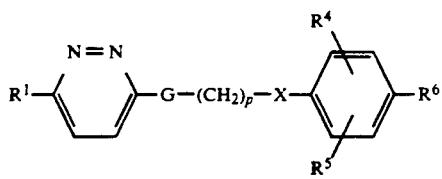

| Comp. No. | R¹ | G | p | X | R⁴ | R⁵ | R⁶ | mp. (°C.)/salt |
|---|---|---|---|---|---|---|---|---|
| 49 | Cl— | —N-piperidyl-OH | 1 | —O— | —H | —H | —COOC$_2$H$_5$ | 152.9 |
| 50 | —CF$_3$ | —N-piperidyl- | 2 | —O— | —H | —H | —COOC$_2$H$_5$ | 110.1 |
| 51 | —CH$_3$ | —N-piperidyl- | 2 | —O— | —H | —H | —COOCH$_2$-c-C$_3$H$_5$ | 119.7 |
| 52 | —C$_2$H$_5$ | —N-piperidyl- | 2 | —O— | —H | —H | —COOC$_2$H$_5$ | 88.4 |
| 53 | Cl— | —N-piperidyl- | 2 | —O— | —H | —H | —CH(OH)CH$_3$ | 84.8 |
| 54 | n-C$_3$H$_7$ | —N-piperidyl- | 2 | —O— | —H | —H | —COOC$_2$H$_5$ | 84.4 |
| 55 | —CH$_3$ | —N-piperidyl- | 1 | —O— | —H | —H | —COOCH$_2$-c-C$_3$H$_5$ | |
| 56 | Cl— | —N-piperidyl- | 2 | —S— | —H | —H | —COOC$_2$H$_5$ | |
| 57 | i-C$_3$H$_7$ | —N-piperidyl- | 2 | —O— | —H | —H | —COOC$_2$H$_5$ | |
| 58 | t-C$_4$H$_9$ | —N-piperidyl- | 2 | —O— | —H | —H | —COOC$_2$H$_5$ | |
| 59 | —CH$_3$ | —N-piperidyl- | 2 | —O— | —H | —H | oxazoline-CH$_2$OH | |

-continued

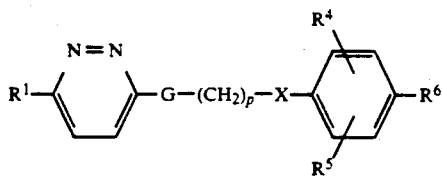

| Comp. No. | R¹ | G | p | X | R⁴ | R⁵ | R⁶ | mp. (°C.)/salt |
|---|---|---|---|---|---|---|---|---|
| 60 | —CH₃ | —N⟨ ⟩ (pyrrolidinyl) | 2 | —O— | —H | —H | —N=C(CH₃)—O—CH(CH₃)—CH₃ (oxazoline) | |
| 61 | —C₂H₅ | —N⟨ ⟩ (pyrrolidinyl) | 2 | —NH— | —H | —H | —COOC₂H₅ | |
| 62 | —C₂H₅ | —N⟨ ⟩ (piperidinyl) | 2 | —O— | 2-Cl | 5-Cl | —COOC₂H₅ | |
| 63 | —C₂H₅ | —N⟨ ⟩ (piperidinyl) | 2 | —O— | 2-CH₃ | —H | —COOC₂H₅ | |
| 64 | —C₂H₅ | —N⟨ ⟩ (piperidinyl) | 2 | —O— | —H | —H | —N=C(CH₃)—O—CH₂—CH(CH₃)—CH₃ | |

* = (Z)-2-butenedioate(1:1)

In the similar manner there were also prepared
ethyl 4-[2-[1-(6-chloro-3-pyridazinyl)-4-piperidinyl]-propoxy]benzoate; mp. 84.9° C. (comp. 65);
ethyl 4-[2-[1-(6-chloro-5-methyl-3-pyridazinyl)-4-piperidinyl]ethoxy]benzoate; mp. 134.1° C. (comp. 66); and
ethyl 4-[2-[1-(6-chloro-4,5-dimethyl-3-pyridazinyl)-4-piperidinyl]ethoxy]benzoate; (comp. 67).

In the similar manner there are also prepared
3-[4-[[4-(4,5-dihydro-4,4-dimethyl-2-oxazolyl)phenyl]-methyl]-1-piperidinyl]-6-methylpyridazine (comp. 68);
3-[4-[3-[4-(4,5-dihydro-2-oxazolyl)phenyl]propyl]-1-piperidinyl]-6-methylpyridazine (comp. 69);
(cyclopropylmethyl) 4-[2-[1-(6-methyl-3-pyridazinyl)-4-piperidinyl]propoxy]benzoate (comp. 70);
(2-ethoxyethyl) 4-[3-[1-(6-chloro-3-pyridazinyl)-4-piperidinyl]propyl]benzoate (comp. 71); and
(cyclopropylmethyl) 4-[2-[4-hexahydro(6-methyl-3-pyridazinyl)-1H-1,4-diazepin-1-yl]ethoxy]benzoate (comp. 72)

EXAMPLE 26

A mixture 1.2 parts of 2,6-difluoropyridazine, 4 parts of ethyl 4-[2-(4-piperidinyl)-ethoxy]benzoate butanedioate(1:1), 5.3 parts of sodium carbonate and 141 parts of N,N-dimethylformamide was stirred for 48 hours at 60° C. After cooling, the reaction mixture was poured into water. The precipitated product was filtered off, washed with water and dissolved in trichloromethane. The organic layer was dried, filtered and evaporated. The residue was crystallized from 2-propanol. The product was filtered off and dried, yielding 2.4 parts (64.3%) of ethyl 4-[2-[1-(6-fluoro-3-pyridazinyl)-4-piperidinyl]ethoxy]benzoate; mp. 131.9° C. (comp. 73).

In a similar manner there was also prepared:
ethyl 4-[3-[1-(6-fluoro-3-pyridazinyl)-4-piperidinyl]-propoxy]benzoate; mp. 106.8° C. (comp. 74)

EXAMPLE 27

A mixture of 4.1 parts of 3,6-dibromopyridazine, 4.34 parts of 1-[3-[4-(4,5-dihydro-2-oxazolyl)phenoxy]-propyl]piperazine, 6.4 parts of sodium carbonate and 188 parts of N,N-dimethylformamide was stirred overnight at 65° C. The reaction mixture was poured into ice water and the product was extracted with dichloromethane. The extract was dried, filtered and evaporated. The residue was purified by column chromatography over silica gel using a mixture of trichloromethane and methanol (98.5:1.5 by volume) as eluent. The pure fractions were collected and the eluent was evaporated. The residue was crystallized from 2-propanol. The product was filtered off and dried, yielding 1.1 parts (16.4%) of 3-bromo-6-[4-[3-[4-(4,5-dihydro-2-oxazolyl)phenoxy]propyl]-1-piperazinyl]pyridazine; mp. 169.1° C. (comp. 75).

In a similar manner there were also prepared:
ethyl 4-[2-[1-(6-bromo-3-pyridazinyl)-4-piperidinyl]ethoxy]benzoate; mp. 122.3° C. (comp. 76); and
ethyl 4-[3-[1-(6-bromo-3-pyridazinyl)-4-piperidinyl]-propoxy]benzoate; mp. 130.0° C. (comp. 77).

EXAMPLE 28

A mixture of 3,6-diiodopyridazine, 4 parts of ethyl 4-[2-(4-piperidinyl)ethoxy]benzoate butanedioate(1:1), 5.3 parts of sodium carbonate and 75 parts of N,N-dimethylformamide was stirred overnight at 65° C. The reaction mixture was poured into 150 parts of water. The precipitated product was filtered off, washed with water and dissolved in dichloromethane. The organic layer was dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2-propanol. The product was filtered off and dried, yielding 2 parts (41.6%) of ethyl 4-[2-[1-(6-iodo-3-pyridazinyl)-4-piperazinyl]ethoxy]benzoate; mp. 122.7° C. (comp. 78).

In a similar manner there were also prepared:
3-[4-[3-[4-(4,5-dihydro-2-oxazolyl)phenoxy]propyl]-1-piperazinyl]-6-iodopyridazine; mp. 170.0° C. (comp. 79); and
ethyl 4-[3-[1-(6-iodo-3-pyridazinyl)-4-piperidinyl]propoxy]benzoate; mp. 139.2° C. (comp. 80).

EXAMPLE 29

A mixture of 2.1 parts of 3-chloro-6-(4-fluorophenyl)-pyridazine, 2.9 parts of ethyl 4-[3-(4-piperidinyl)propoxy]benzoate, 1.1 parts of sodium carbonate and 2 parts of N,N-dimethylacetamide was stirred for 2 hours in an oil bath at 140° C. The reaction mixture was diluted with water while cooling. The precipitated product was filtered off, washed with water and dissolved in trichloromethane. The organic layer was dried, filtered and evaporated. The residue was crystallized from 2-propanol. The product was filtered off and dried, yielding 3.4 parts (73.3%) of ethyl 4-[3-[1-[6-(4-fluorophenyl)-3-pyridazinyl]-4-piperidinyl]propoxy]benzoate; mp. 160.4° C. (comp. 81).

In a similar manner there was also prepared:
ethyl 4-[2-[1-[6-(4-fluorophenyl)-3-pyridazinyl]-4-piperidinyl]ethoxy]benzoate; mp. 154.9° C. (comp. 82).

EXAMPLE 30

A mixture of 2.4 parts of 3-chloro-6-(methylthio)-pyridazine, 4.5 parts of 1-[3-[4-(4,5-dihydro-2-oxazolyl)-phenoxy]propyl]piperazine, 1.6 parts of sodium carbonate and 80 parts of 1-butanol was stirred for 5 days at reflux temperature. The reaction mixture was evaporated and the residue was dissolved in trichloromethane. The organic phase was washed with water, dried, filtered and evaporated. The residue was purified by column chromatography over silica gel using a mixture of trichloromethane and methanol (97:3 by volume) as eluent. The pure fractions were collected and the eluent was evaporated. The residue was crystallized from 2-propanol. The product was filtered off and dried, yielding 0.7 parts (11.2%) of 3-[4-[3-[4-(4,5-dihydro-2-oxazolyl)phenoxy]propyl]-1-piperazinyl]-6-(methylthio)pyridazine; mp. 163.1° C. (comp. 83).

EXAMPLE 31

A mixture of 2.4 parts of 3-butyl-6-chloropyridazine, 4.2 parts of ethyl 4-[2-(4-piperidinyl)ethoxy]benzoate and 2.1 parts of sodium carbonate was stirred for 4 hours at 140° C. After cooling, the reaction mixture was taken up in water and dichloromethane. The separated organic layer was dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2,2'-oxybispropane. The product was filtered off, washed with 2,2'-oxybispropane and dried at 50° C., yielding 1.2 parts (20.8%) of ethyl 4-[2-[1-(6-butyl-3-pyridazinyl)-4-piperidinyl]ethoxy]benzoate; mp. 91.4° C. (comp. 84).

In a similar manner there was also prepared:
ethyl 4-[2-[1-(6-ethyl-3-pyridazinyl)-4-piperidinyl]ethoxy]benzoate; mp. 88.4° C. (comp. 85)

EXAMPLE 32

A mixture of 4 parts of 3,8-dichlorophthalazine, 4.2 parts of ethyl 4-[2-(4-piperidinyl)ethoxy]benzoate, 4 parts of sodium hydrogen carbonate and 120 parts of ethanol was stirred and refluxed overnight. After evaporation, the residue was taken up in water and dichloromethane. The organic layer was dried, filtered and evaporated. The residue was purified by column chromatography over silica gel using trichloromethane and methanol (98:2 by volume) as eluent. The pure fractions were collected and the eluent was evaporated. The residue was converted into the hydrochloride salt in 2-propanol. The salt was filtered off, washed with 2-propanol and 2,2'-oxybispropane and dried at 50° C., yielding 3.3 parts (46.2%) of ethyl 4-[2-[1-(8-chloro-3-phthalazinyl)-4-piperidinyl]ethoxy]benzoate monohydrochloride; mp. 172.4° C. (comp. 86).

EXAMPLE 33

A mixture of 5 parts of 1-(3-chloropropoxy)-4-methoxybenzene, 3.9 parts of 3-chloro-6-(1-piperazinyl)pyridazine, 8.5 parts of sodium carbonate and 188 parts of N,N-dimethylformamide was stirred overnight at about 65° C. The reaction mixture was poured into ice water and the product was extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from 2-propanol. The product was filtered off and dried, yielding 4.9 parts (67.5%) of 3-chloro-6-[4-[3-(4-methoxyphenoxy)propyl]-1-piperazinyl]pyridazine; mp. 122.9° C. (comp. 87).

In a similar manner there were also prepared:

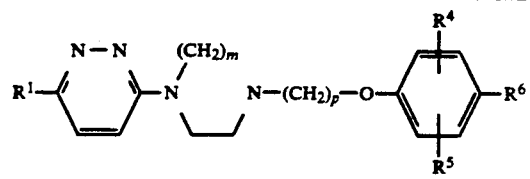

| Comp. No. | R¹ | m | p | R⁴ | R⁵ | R⁶ | Salt/ mp. (°C.) |
|---|---|---|---|---|---|---|---|
| 88 | —OCH₃ | 2 | 3 | H | H | 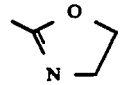 | 151.4 |

-continued

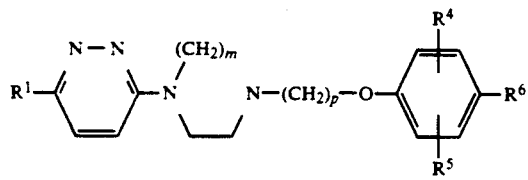

| Comp. No. | R¹ | m | p | R⁴ | R⁵ | R⁶ | Salt/ mp. (°C.) |
|---|---|---|---|---|---|---|---|
| 89 | Cl— | 2 | 2 | H | H | (N,N-dimethyl oxazoline) | 137.5 |
| 90 | Cl— | 2 | 3 | H | H | (oxazoline) | 160.3 |
| 91 | Cl— | 3 | 3 | H | H | (oxazoline) | 119.2 |
| 92 | Cl— | 2 | 4 | 2-Cl | H | —OCH₃ | 89.8 |
| 93 | Cl— | 2 | 3 | 2-Cl | 5-Cl | —OCH₃ | 171.0 |
| 94 | Cl— | 2 | 3 | H | H | —COOC₂H₅ | 125.8 |
| 95 | Cl— | 2 | 3 | 2-Cl | 3-Cl | —OCH₃ | 145.1 | and
3-chloro-6-[4-[3-[4-(4,5-dihydro-2-oxazolyl)phenoxy]-propyl]-3-methyl-1-piperazinyl]pyridazine; mp. 131.1° C. (comp. 96); and ethyl 4-[3-[[2-[(6-chloro-3-pyridazinyl)amino]ethyl-]amino]propoxy]benzoate (E)-2-butenedioate(1:1); mp. 156.7° C. (comp. 97).

EXAMPLE 34

A mixture of 2 parts of 3-chloro-6-(1-piperazinyl)-pyridazine, 2 parts of 4-formylbenzoic acid, 2 parts of a thiophene solution 4%, 1.5 parts of N,N-diethylethana-mine and 80 parts of methanol was hydrogenated at normal pressure and at room temperature with 2 parts of platinum-on-charcoal catalyst 5%. After the calculated amount of hydrogen was taken up, the catalyst was filtered off and the filterate was evaporated. The residue was converted into the hydrochoride salt in 2-propanol. The precipitated product was filtered off, washed with 2-propanol and 2,2'-oxybispropane and dried at 50° C., yielding 1.3 parts (35.2%) of 4-[[4-(6-chloro-3-pyridazinyl)-1-piperazinyl]methyl]benzoic acid monohydrochloride; mp.>300° C. (comp. 98).

EXAMPLE 35

A mixture of 4.1 parts of 3-choro-6-[4-(3-chloro-propyl)-1-piperidinyl]pyridazine, 2.5 parts of ethyl 3-hydroxybenzoate, 14 parts of potassium carbonate and 94 parts of N,N-dimethylformamide was stirred overnight at 110° C. The reaction mixture was evaporated and the residue was taken up in water and dichloro-methane. The separated organic layer was dried, filtered and evaporated. The residue was crystallized from 2-propanol. The product was filtered off, washed with 2-propanol and 2,2'-oxybispropane and dried at 50° C., yielding 4.6 parts (75.9%) of ethyl 3-[3-[1-(6-chloro-3-pyridazinyl)-4-piperidinyl]propoxy]benzoate; mp. 105.3° C. (comp. 99).

In a similar manner there were also prepared:

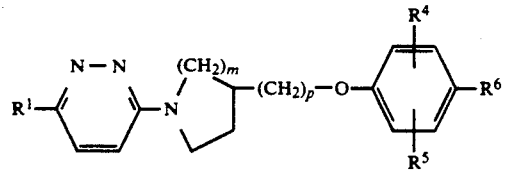

| Comp. No. | R¹ | m | p | R⁴ | R⁵ | R⁶ | Salt/m.p. (°C.) |
|---|---|---|---|---|---|---|---|
| 100 | Cl— | 1 | 2 | H | H | —COOC₂H₅ | 131.3 |
| 101 | Cl— | 2 | 3 | H | H | —COOCH₃ | 142.5 |
| 102 | Cl— | 2 | 2 | H | H | —COOC₂H₅ | 114.2 |
| 103 | Cl— | 2 | 1 | H | H | —COOC₂H₅ | 148.9 |
| 104 | Cl— | 2 | 3 | 2-COOC₂H₅ | H | H | 89.0 |
| 105 | Cl— | 2 | 1 | 2-Cl | 6-Cl | (oxazoline) | 137.3 |
| 106 | Cl— | 2 | 3 | H | H | —OCH₃ | 107.3 |
| 107 | Cl— | 2 | 2 | H | H | —CON(CH₃)₂ | 141.9 |
| 108 | Cl— | 2 | 2 | H | H | —COOCH₂CH=CH₂ | 90.6 |
| 109 | —OCH₃ | 2 | 2 | H | H | —COOCH₂CH₃ | 114.9 |
| 110 | Cl— | 2 | 2 | H | H | —COH | 124.8 |
| 111 | —OH | 2 | 3 | H | H | —COOCH₂CH₃ | 171.8 |
| 112 | Cl— | 2 | 2 | H | H | —CONH₂ | 231.0 |
| 113 | —OCH₃ | 2 | 3 | H | H | —COOCH₂CH₃ | 169.6 |
| 114 | Cl— | 2 | 3 | H | H | —NO₂ | 164.7 |
| 115 | Cl— | 2 | 2 | H | H | —COO(CH₂)₂N(CH₃)₂ | 125.9 |
| 116 | Cl— | 2 | 2 | H | H | —NO₂ | 150.3 |
| 117 | —OCH₃ | 1 | 2 | H | H | —COOCH₂CH₃ | 97.0 |
| 118 | —OH | 2 | 2 | H | H | —COOCH₂CH₃ | 168.1 | and ethyl 4-[2-[8-(6-chloro-3-pyridazinyl)-8-azabicyclo[3.2.-1]octan-3-yl]ethoxy]benzoate; mp. 132.1° C. (comp. 119).

EXAMPLE 36

A mixture of 3.9 parts of 3-chloro-6-[4-(2-chloroethyl)-1-piperidinyl]pyridazine, 2.64 parts of (2-propynyl) 4-hydroxybenzoate, 2.76 parts of potassium carbonate and 75 parts of N,N-dimethylacetamide was stirred overnight at 110° C. After cooling, the reaction mixture was poured into 100 parts of water and the product was extracted with methylbenzene. The extract was dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2-propanol. The product was filtered off and dried, yielding 5.2 parts (86.7%) of (2-propynyl) 4-[2-[1-(6-chloro-3-pyridazinyl)-4-piperidinyl]ethoxy]benzoate; mp. 122.0° C. (comp. 120).

In a similar manner there were also prepared:

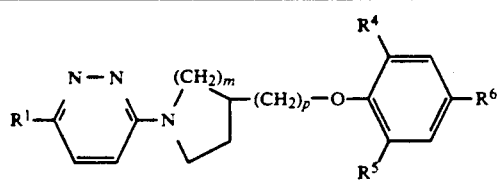

| Comp. No. | R¹ | m | p | R⁴ | R⁵ | R⁶ | Salt/ mp. (°C.) |
|---|---|---|---|---|---|---|---|
| 121 | Cl— | 2 | 3 | H | H | —COOC₃H₇ | 128.8 |
| 122 | Cl— | 2 | 3 | H | H | —COOC₄H₉ | 110.7 |
| 123 | Cl— | 1 | 1 | H | H | —COOC₂H₅ | 135.0 |
| 124 | Cl— | 2 | 3 | Cl | Cl | —COOC₂H₅ | 79.2 |
| 125 | Cl— | 2 | 2 | H | H | —CN | 149.0 |
| 126 | Cl— | 2 | 2 | H | H | —COOC₂H₄—OCH₃ | 88.4 |
| 127 | Cl— | 2 | 2 | H | H | —COOCH₂—C₆H₅ | 133.4 |
| 128 | —CH₃ | 2 | 3 | H | H | —COOCH₂—CH=CH₂ | 161.9/ HCl |

EXAMPLE 37

A mixture of 2.6 parts of 3-chloro-6-[4-(2-chloroethyl)-1-piperidinyl]pyridazine, 1.9 parts of (cyclopropylmethyl) 4-hydroxybenzoate 1.1 parts of sodium carbonate and 94 parts of N,N-dimethylacetamide was stirred overnight at 110° C. After cooling, the reaction mixture was poured into water. The precipitated product was filtered off, washed with water and dissolved in trichloromethane. The organic layer was dried, filtered and evaporated. The residue was crystallized from 2-propanol. The product was filtered off and dried, yielding 2.9 parts (69.7%) of (cyclopropylmethyl) 4-[2-[1-(6-chloro-3-pyridazinyl)-4-piperidinyl]ethoxy]benzoate; mp. 134.0° C. (comp. 129).

In a similar manner there were also prepared:

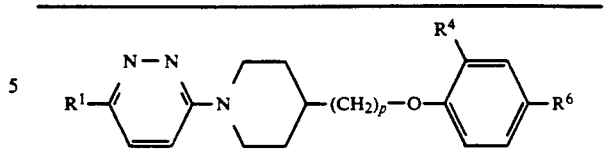

| Comp. No. | R¹ | p | R⁴ | R⁶ | salt/ mp. (°C.) |
|---|---|---|---|---|---|
| 130 | Cl— | 3 | Cl— | —COOCH₂—CH₃ | 144.7 |
| 131 | Cl— | 4 | —H | —COOCH₂—CH₃ | 85.9 |
| 132 | Cl— | 2 | —H | —COCH₃ | 115.7 |
| 133 | Cl— | 2 | —H | —COOCH(CH₃)₂ | 104.4 |
| 134 | Cl— | 2 | —H | —COOC₂H₄OC₂H₅ | 91.4 |
| 135 | Cl— | 3 | —H | —CF₃ | 119.1 |
| 136 | Cl— | 2 | —H | —CF₃ | 126.0 |
| 137 | —CH₃ | 2 | —H | —COOCH₂—CH=CH₂ | 119.1/ H₂O/* |
| 138 | —CH₃ | 3 | —H | —COOCH₂-c-C₃H₅ | 114.9 |
| 139 | —CH₃ | 1 | —H | —COOCH₂—CH=CH₂ | 132.6 |

*(Z)-2-butenedioate(1:1)

and
ethyl 4-[2-[1-(6-chloro-3-pyridazinyl)-3-piperidinyl]ethoxy]benzoate; mp. 86.9° C. (comp. 140).

EXAMPLE 38

To a stirred solution of 3.0 parts of 3-chloro-6-[4-(3-chloropropyl)-1-piperidinyl]pyridazine in 80 parts of acetonitrile were added 2.1 parts of sodium iodide. The reaction mixture was stirred for 2 hours at reflux temperature. After cooling, a mixture of 2.2 parts of 2-chloro-4-methoxyphenol and 3.8 parts of potassium carbonate was added to the mixture and the whole was stirred for 2 days at reflux temperature. The reaction mixture was evaporated and the residue was taken up in water. The product was extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from 2-propanol. The product was filtered off and dried at 70° C., yielding 1.8 parts (41.3%) of 3-chloro-6-[4-[3-(2-chloro-4-methoxyphenoxy)propyl]-1-piperidinyl]pyridazine; mp. 101.0° C. (comp. 141).

EXAMPLE 39

To a stirred and cooled solution of 6.7 parts of 1-(6-methoxy-3-pyridazinyl)-4-piperidinemethanol, 5 parts of ethyl 4-hydroxybenzoate and 7.8 parts of triphenylposphine in 135 of tetrahydrofuran was added a solution of 5.6 parts of diethyl diazenedicarboxylate in 45 parts of tetrahydrofuran. Upon complete addition, stirring was continued overnight at room temperature. After evaporation, the residue was taken up in water and the product was extracted with dichloromethane. The extract was dried, filtered and evaporated. The residue was purified by column chromatography over silica gel using a mixture of trichloromethane and ethanol (99.5:0.5 by volume) as eluent. The pure fractions were collected and the eluent was evaporated. The residue was crystallized from 2-propanol. The product was filtered off and dried, yielding 6.7 parts (60.1%) of ethyl 4-[[1-(6-methoxy-3-pyridazinyl)-4-piperidinyl]methoxy]benzoate; mp. 147.2° C. (comp. 142).

In a similar manner there were also prepared:

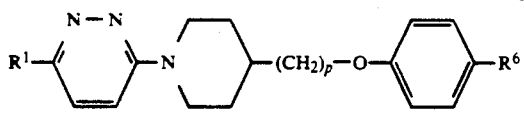

| Comp. No. | R¹ | p | R⁶ | salt/mp. (°C.) |
|---|---|---|---|---|
| 143 | Cl— | 2 | —OCOC$_2$H$_5$ | 128.1 |
| 144 | Cl— | 3 | —OCOC$_2$H$_5$ | 137.2 |
| 145 | Cl— | 2 | —C$_6$H$_5$ | 127.5 |
| 146 | —CH$_3$ | 3 | —COOCH$_3$ | 136.5 |
| 147 | —CH$_3$ | 2 | —COOCH(CH$_3$)$_2$ | 141.9/HCl/H$_2$O |
| 148 | —CH$_3$ | 2 | —COOCH$_3$ | 131.2 |
| 149 | —CH$_3$ | 1 | —COOCH(CH$_3$)$_2$ | 148.0 |
| 150 | —CH$_3$ | 1 | —COOCH$_3$ | 155.7 |
| 151 | —CH$_3$ | 1 | —COOC$_2$H$_5$ | 130.7 |
| 152 | Cl— | 1 | —C$_6$H$_5$ | 180.0 |
| 153 | Cl— | 3 | —C$_6$H$_5$ | 167.2 |
| 154 | —CH$_3$ | 3 | —COOCH(CH$_3$)$_2$ | 114.0/HCl/H$_2$O |
| 155 | —CH$_3$ | 1 | —COOC$_2$H$_4$OCH$_3$ | 110.4 |
| 156 | —CH$_3$ | 2 | —COOC$_2$H$_4$OCH$_3$ | 171.1 |
| 157 | —CH$_3$ | 3 | —COOC$_2$H$_4$OCH$_3$ | 94.3/HCl/H$_2$O |
| 158 | Cl— | 1 | —CF$_3$ | 157.8 |
| 159 | Cl— | 3 | —NHCOOC$_2$H$_5$ | 158.4 |
| 160 | Cl | 2 | —COOC$_6$H$_5$ | 145.2 |
| 161 | —Cl— | 2 | —COOC$_3$H$_7$ | 110.8 |
| 162 | —CH$_3$ | 2 | —COOC$_3$H$_7$ | 106.4/H$_2$O/(Z)-2-butenedioate(1:1) |
| 163 | —C$_6$H$_5$ | 2 | —C$_6$H$_5$ | |

EXAMPLE 40

To a stirred solution of 5.6 parts of 1-(6-chloro-3-pyridazinyl)-4-piperidinepropanol, 4.2 parts of ethyl 4-mercaptobenzoate and 6 parts of triphenylposphine in 135 parts of tetrahydrofuran was added dropwise a solution of 4 parts of diethyl diazenedicarboxylate in 45 parts of tetrahydrofuran at 20° C. Upon complete addition, stirring was continued overnight at this temperature. The reaction mixture was evaporated and the residue was taken up in water. The product was ectracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from 2,2'-oxybispropane. The product was filtered off and dried, yielding 1.3 parts (13.5%) of ethyl 4-[[3-[1-(6-chloro-3-pyridazinyl)-4-piperidinyl]propyl]thio]benzoate; mp. 96.3° C. (comp. 164).

EXAMPLE 41

To a stirred mixture of 7 parts of ethyl 4-[[1-(6-chloro-3-pyridazinyl)-4-hydroxy-4-piperidinyl]methoxy]benzoate and 150 parts of ethyl acetate were added dropwise 8.4 parts of thionyl chloride. Upon complete addition, stirring was continued first overnight at room temperature and then for 1 hour at 65° C. The reaction mixture was evaporated and the residue was taken up in water. The whole was treated with concentrated ammonium hydroxide and the product was extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from 2-propanol. The product was filtered off and dried, yielding 1.8 parts (26.7%) of ethyl 4-[[1-(6-chloro-3-pyridazinyl)-1,2,3,6-tetrahydro-4-pyridinyl]methoxy]benzoate; mp. 161.7° C. (comp. 165).

EXAMPLE 42

To a stirred solution of 4.5 parts of potassium hydroxide in 50 parts of water was added dropwise a solution of 4 parts of ethyl 4-[3-[1-(6-chloro-3-pyridazinyl)-4-piperidinyl]propoxy]benzoate in 160 parts of ethanol. Upon complete addition, stirring was continued over weekend at room temperature. The precipitated product was filtered off, washed with water and then stirred in water. The whole was neutralized with acetic acid. The product was filtered off, washed with water and converted into the hydrochloride salt in methanol. The crystallized product was filtered off and the filtrate was evaporated. The residue and the crystallized product were combined and stirred into water and sodium hydroxide. The precipitate was filtered off and the filtrate was treated with acetic acid. The precipitated product was filtered off, washed with water and crystallized from N,N-dimethylformamide. The product was filtered off and dried, yielding 0.7 parts (18.6%) of 4-[3-[1-(6-chloro-3-pyridazinyl)-4-piperidinyl]propoxy]benzoic acid; mp. 209.4° C. (comp. 166).

EXAMPLE 43

A mixture of 16.7 parts of ethyl 4-[[4-(6-chloro-3-pyridazinyl)-1-piperazinyl]methyl]benzoate and 11.3 parts of 2-hydroxyethanamine was stirred for 4 hours at 140° C. After cooling, the reaction mixture was stirred into water. The precipitated product was filtered off, washed with 2,2'-oxybispropane and converted into the hydrochloride salt in 2-propanol. The salt was filtered off, washed with 2-propanol and 2,2'-oxybispropane and dried at 70° C., yielding 9.7 parts (51.1%) of 4-[[4-(6-chloro-3-pyridazinyl)-1-piperazinyl]methyl]-N-(2-hydroxyethyl)benzamide monohydrochloride; mp. >260° C. (decomp.) (comp. 167).

EXAMPLE 44

To a stirred and cooled mixture of 10 parts of 4-[[1-(6-chloro-3-pyridazinyl)-4-hydroxy-4-piperidinyl]methoxy]-N-(2-hydroxyethyl)benzamide and 228 parts of ethyl acetate were added dropwise 8.4 parts of thionyl chloride. Upon complete addition, stirring was continued first overnight at room temperature and then for 1 hour at 60° C. The reaction mixture was evaporated and the residue was dissolved in a solution of 20 parts of sodium hydrogen carbonate in 160 parts of ethanol. The whole was stirred overnight at reflux temperature. After evaporation, the residue was taken up in water. The precipitated product was filtered off and purified by column chromatography over silica gel using a mixture of trichloromethane and methanol (98:2 by volume) as eluent. The pure fractions were collected and the eluent was evaporated. The residue was crystallized from 2-propanol. The product was filtered off and dried, yielding 1 part (10.7%) of 3-chloro-6-[4-[[4-(4,5-dihydro-2-oxazolyl)phenoxy]methyl]-3,6-dihydro-1(2H)-pyridinyl]pyridazine; mp. 176.0° C. (comp. 168).

EXAMPLE 45

A mixture of 3.8 parts of 3-chloro-6-[4-[3-[4-(4,5-dihydro-2-oxazolyl)phenoxy]propyl]-1-piperazinyl]-pyridazine, 200 parts of methanol and 2 parts of calcium oxide was hydrogenated at normal pressure and at 50° C. with 2 parts of palladium-on-charcoal catalyst 10%.

After the calculated amount of hydrogen was taken up, the catalyst was filtered off and the filtrate was evaporated. The residue was taken up in water and the product was extracted with dichloromethane. The extract was dried, filtered and evaporated. The residue was purified by column chromatography over silica gel using a mixture of trichloromethane and methanol (96:4 by volume) as eluent. The pure fractions were collected and the eluent was evaporated. The residue was crystallized from 2-propanol. The product was filtered off, washed with 2-propanol and 2,2'-oxybispropane and dried over weekend at 60° C., yielding 0.7 parts (17.2%) of 3-[4-[3-[4-(4,5-dihydro-2-oxazolyl)phenoxy]propyl]-1-piperazinyl]pyridazine; mp. 144.7° C. (comp. 169).

In a similar manner there were also prepared:
ethyl 4-[2-[1-(3-pyridazinyl)-4-piperidinyl]ethoxy]benzoate; mp. 93.2° C. (comp. 170).
ethyl 4-[3-[1-(3-pyridazinyl)-4-piperidinyl]propoxy]benzoate; mp. 96.5° C. (comp. 171).

C. BIOLOGICAL EXAMPLES

The strong antiviral activity of the compounds of formula (I) is clearly evidenced by the data obtained in the following experiment, which data are only given to illustrate the useful antiviral properties of all the compounds of formula (I) and not to limit the invention either with respect to the scope of susceptible viruses nor with respect to the scope of formula (I).

EXAMPLE 46: Picornavirus Minimal Inhibitory Concentration Test

The Minimal Inhibitory Concentration of the compounds of the present invention against the Human Rhinovirus strains (HRV)-2,-9,-14,-15,-29,-39,-41,-42,-45,-51,-59,-63,-70,-72,-85,-86 and -89 was determined by a standard cytopathic effect reduction assay as follows. To each of the ninty six (96) wells of a microtiter 96 well tissue culture plate there was added 60 μl of a Ohio Hela cell maintenance medium [Eagle's Basal medium supplemented with 5% Foetal Calf Serum (FCS)].

To two wells there was added 60 μl of an appropriate starting dilution of a compound of formula (I) and twofold dilutions were made to cover a wide range of compound concentrations. Subsequently there were added 120 μl of an infectious solution of virus in Eagle's Basal Medium with 2% Hepes buffer, 2% FCS and 30 mM $MgCl_2$ to all wells except cell and compound controls. Said infectious virus solution having a $TCID_{50}$-value (Tissue Culture Infectious Dose) of about 100.

The $TCID_{50}$-value is the dose of viruses which initiates a cytopathic effect in 50% of the inoculated cells. 150 μl of the thus obtained virus-compound mixtures were then transferred to microtitre plates with subconfluent Ohio Hela Cells, grown in 100 μl of maintenance medium. Appropriate virus controls, cell controls and compound controls were included in each test. Plates were incubated for 3 to 5 days at 33° C. in 5% $CO_2$ atmosphere. They were checked daily by light microscopy without staining and read when the virus controls showed 100% cytopathic effect (CPE) and the virus back titration confirmed that a $TCID_{50}$-value between 32 and 256 had been used in the test. The $IC_{50}$-value for each virus-compound series was taken as the concentration in ng/ml that protected 50% of the cells from cytopathic effects with respect to the untreated controls. In the standard test procedure, the compounds were tested against two panels of rhinoviruses, a first panel consisting of serotypes HRV-2,-29,-39,-85,-9,-15,-51,-59,-63,-89,-44 and the other panel consisting of HRV-42,-45,-14,-70,-72 and -86.

The $IC_{50}$-value for each rhinovirus serotype was determined, and the efficacy of each compound was determined in terms of the $Med_1$-value and $Med_2$-value, which is the medium value of the $IC_{50}$-values of all serotypes from the first and second panel respectively.

The following table gives the testing results with the compounds of the invention.

| Activity of antirhinoviral compounds | | |
|---|---|---|
| Comp. No. | $Med_1$ (ng/ml) | $Med_2$ (ng/ml) |
| 1 | 2 | 39 |
| 7 | 725 | 404 |
| 8 | 750 | 21 |
| 23 | 13 | 119 |
| 24 | 675 | 115 |
| 33 | 55 | 142 |
| 34 | 6 | 81 |
| 35 | 1 | 294 |
| 38 | 6 | 97 |
| 42 | 86 | 188 |
| 47 | 100 | 250 |
| 50 | 63 | 24 |
| 73 | 11 | 750 |
| 74 | 27 | 102 |
| 76 | 2 | 110 |
| 77 | 25 | 125 |
| 78 | 3 | 103 |
| 80 | 25 | 200 |
| 92 | 213 | 125 |
| 94 | 163 | 69 |
| 95 | 350 | 838 |
| 100 | 12 | 139 |
| 101 | 108 | 225 |
| 102 | 3 | 53 |
| 103 | 7 | 694 |
| 108 | 5 | 181 |
| 109 | 6 | 42 |
| 117 | 12 | 132 |
| 119 | 175 | 850 |
| 121 | 44 | 678 |
| 129 | 23 | 175 |
| 131 | 21 | 161 |
| 133 | 50 | 175 |
| 137 | 6 | 113 |
| 138 | 50 | 188 |
| 142 | 13 | 650 |
| 145 | 6 | 188 |
| 146 | 100 | 86 |
| 147 | 88 | 105 |
| 148 | 12 | 225 |
| 149 | 50 | 172 |
| 154 | 100 | 102 |
| 162 | 6 | 23 |
| 165 | 8 | 29 |
| 170 | 4 | — |
| 171 | 27 | 59 |

D. COMPOSITION EXAMPLES

The following formulations exemplify typical pharmaceutical compositions in dosage unit form suitable for systemic administration to animal and human subjects in accordance with the present invention.

"Active ingredient" (A.I.) as used throughout these examples relates to a compound of formula (I), a pharmaceutically acceptable acid addition salt or a stereochemically isomeric form thereof.

EXAMPLE 47: ORAL DROPS 500 g of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 0.01 g of the A.I. per ml. The resulting solution was filled into suitable containers.

EXAMPLE 48: ORAL SOLUTION 9 g of methyl 4-hydroxybenzoate and 1 part of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propanetriol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 0.005 g of the A.I. per teaspoonful (5 ml). The resulting solution was filled in suitable containers.

EXAMPLE 49: CAPSULES 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 0.02 g of the A.I.

EXAMPLE 50: FILM-COATED TABLETS

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10,000 tablets, each comprising 0.01 g of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109 ®) and the whole was homogenated. The tablet cores were coated with the thus obtained mixture in a coating apparatus.

EXAMPLE 51: INJECTABLE SOLUTION 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 0.004 g A.I. per ml. The solution was sterilized by filtration (U.S.P. XVII p. 811) and filled in sterile containers.

EXAMPLE 52: SUPPOSITORIES 3 g A.I. was dissolved in a solution of 3 g 2,3-dihydroxy-butanedioic acid in 25 ml polyethylene glycol 400. 12 G surfactant (SPAN ®) and triglycerides (Witepsol 555 ®) q.s. ad 300 g were molten together. The latter mixture was mixed well with the former solution. The thus obtained mixture was poured into moulds at a temperature of 37°~38° C. to form 100 suppositories each containing 0.03 g of the active ingredient.

EXAMPLE 53: AEROSOLS a) To a solution of 0.1 g of hydroxypropyl β-cyclodextrin (MS=0.43) in 0.7 ml of distilled water were added 730 μg of a 0.1N hydrochloric acid solution and 2.5 mg A.I.. After stirring for 10 minutes at room temperature, the pH of the thus obtained solution was adjusted to pH 5.5 by adding a 0.1N sodium hydroxide solution. Then there were added successively 4 mg of sodium chloride and 0.15 mg of phenyl mercuri acetate and the whole was stirred to produce a complete solution. Distilled water was then added to a volume of 1.0 ml. The whole was filled in a glass bottle closed with a mechanical pump delivering 0.1 ml per puff upon administration.

b) To a solution of 0.1 g of dimethyl β-cyclodextrin in 0.7 ml of distilled water were added 600 μg of a 0.1N hydrochloric acid solution and 2 mg A.I.. After stirring for 10 minutes at room temperature, 10 mg of polyvinylalcohol was dissolved in the mixture and the pH of the thus obtained solution was adjusted to pH 5.5 by adding a 0.1N sodium hydroxide solution. Then there were added successively 4 mg of sodium chloride and 2 mg of phenylethyl alcohol and the whole was stirred to produce a complete solution. Distilled water was added to produce a volume of 1.0 ml which was filled in a glass bottle closed with a mechanical pump spray delivering 0.1 ml per puff upon administration.

We claim:

1. A compound of the formula:

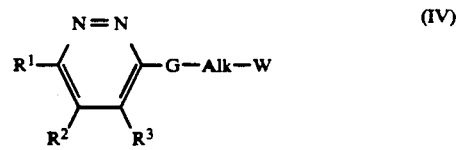

an acid addition salt thereof, or a sterochemically isomeric form thereof, wherein:

Alk represents $C_{1-6}$alkanediyl;

W represents halo or a sulfonyloxy group;

$R^1$ represents hydrogen, $C_{1-4}$alkyl, halo, hydroxy, or $C_{1-4}$alkyl;

$R^2$ and $R^3$ each independently represent hydrogen or $C_{1-4}$alkyl; and

G represents a bivalent group of the formula:

-continued

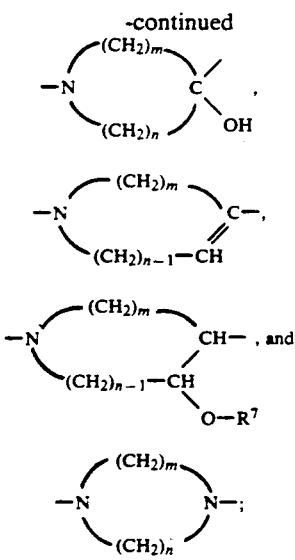

wherein:
one or more carbon atoms within the groups (a-1) through (a-5) may optionally be substituted with $C_{1-6}$alkyl, or two carbon atoms in the groups (a-1) through (a-5) may be bridged with a $C_{2-4}$alkanediyl group;

m and n each independently represent integers within the range of from 1 to 4, inclusive, with the proviso that the sum of m and n in the bivalent groups (a-1) through (a-5) is 4; and $R^7$ represents hydrogen, $C_{1-4}$alkyl, or arylmethyl, wherein in the foregoing aryl represents phenyl, which may optionally be substituted with 1, 2, or 3 substituents each independently selected from halo, $C_{1-6}$alkyl, trifluoromethyl, nitro, amino, $C_{1-6}$alkyloxy, hydroxy, and $C_{1-6}$alkyloxycarbonyl, provided that $R^2$ is unbranched $C_{1-4}$alkyl when $R^1$ or $R^3$ is tert-butyl.

2. A compound according to claim 1 wherein Alk represents $C_{1-4}$alkanediyl.

3. A compound according to claim 2 wherein $R^1$ represents hydrogen, $C_{1-4}$alkyl, or halo.

4. A compound according to claim 3 wherein said compound is 3-[4-(2-chloroethyl)-1-piperidinyl]-6-methylpyridazine.

5. A compound of the formula:

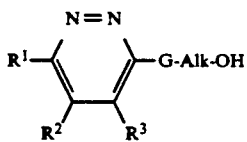

an acid addition salt thereof, or a stereochemically isomeric form thereof, wherein:
Alk represents $C_{1-6}$alkanediyl;
W represents halo or a sulfonyloxy group;
$R^1$ represents hydrogen, $C_{1-4}$alkyl, halo, hydroxy, or $C_{1-4}$alkyl;
$R^2$ and $R^3$ each independently represent hydrogen or $C_{1-4}$alkyl; and
G represents a bivalent group of the formula:

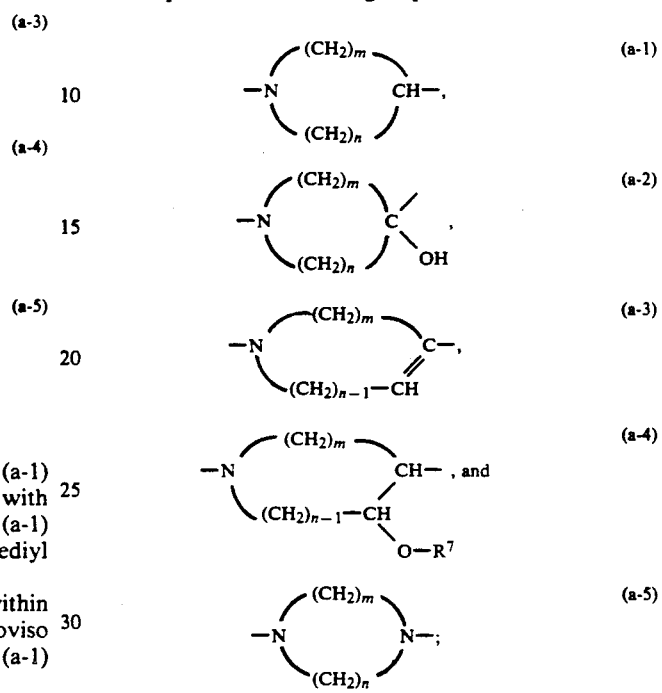

wherein:
one or more carbon atoms within the groups (a-1) through (a-5) may optionally be substituted with $C_{1-6}$alkyl, or two carbon atoms in the groups (a-1) through (a-5) may be bridged with a $C_{2-4}$alkanediyl group;

m and n each independently represent integers within the range of from 1 to 4, inclusive, with the proviso that the sum of m and n in the bivalent groups (a-1) through (a-5) is 4; and $R^7$ represents hydrogen, $C_{1-4}$alkyl, or arylmethyl, wherein in the foregoing aryl represents phenyl, which may optionally be substituted with 1, 2, or 3 substituents each independently selected from halo, $C_{1-6}$alkyl, trifluoromethyl, nitro, amino, $C_{1-6}$alkyloxy, hydroxy, and $C_{1-6}$alkyloxycarbonyl, provided that $R^2$ is unbranched $C_{1-4}$alkyl when $R^1$ or $R^3$ is tert-butyl.

6. A compound according to claim 5 wherein Alk represents $C_{1-4}$alkanediyl.

7. A compound according to claim 6 wherein $R^1$ represents hydrogen, $C_{1-4}$alkyl, or halo.

8. A compound according to claim 7 wherein said compound is 1-(6-methyl-3-pyridazinyl)-4-piperidineethanol.

* * * * *

UNITED STATES PATENT AND TRADEMARK OFFICE
CERTIFICATE OF CORRECTION

PATENT NO. : 5,106,973
DATED : April 21, 1992
INVENTOR(S) : Raymond Stokbroekx, Beerse; Marcel J. M. Van der Aa, Kasterlee; Marcel G. M. Luyckx, Geel; Gilbert A. J. Grauwels, Kessel-Lo, all of Belgium It is certified that error appears in the above-indentified patent and that said Letters Patent is hereby corrected as shown below:

Column 58 at lines 57 and 58 [$R^1$ represents hydrogen, $C_{1-4}$alkyl, halo, hydroxy, or $C_{1-4}$alkyl;] should read "$R^1$ represents hydrogen, $C_{1-4}$alkyl, halo, hydroxy, or $C_{1-4}$alkyloxy"

Column 60 at lines 2 and 3, same as above [$C_{1-4}$alkyl] should read "$C_{1-4}$alkyloxy"

Signed and Sealed this

Seventeenth Day of May, 1994

Attest:

BRUCE LEHMAN

Attesting Officer      Commissioner of Patents and Trademarks